(12) United States Patent
Noguchi

(10) Patent No.: US 10,820,889 B2
(45) Date of Patent: Nov. 3, 2020

(54) ACOUSTIC WAVE IMAGE GENERATING APPARATUS AND METHOD

(71) Applicant: FUJIFILM Corporation, Tokyo (JP)

(72) Inventor: Masafumi Noguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 513 days.

(21) Appl. No.: 15/722,433

(22) Filed: Oct. 2, 2017

(65) Prior Publication Data
US 2018/0042576 A1 Feb. 15, 2018

Related U.S. Application Data

(63) Continuation of application No. PCT/JP2016/058569, filed on Mar. 17, 2016.

(30) Foreign Application Priority Data

Apr. 3, 2015 (JP) .................. 2015-076977

(51) Int. Cl.
*A61B 8/00* (2006.01)
*A61B 8/14* (2006.01)
(Continued)

(52) U.S. Cl.
CPC ............ *A61B 8/463* (2013.01); *A61B 8/0841* (2013.01); *A61B 8/14* (2013.01); *A61B 8/4477* (2013.01); *A61B 8/5207* (2013.01); *A61B 34/20* (2016.02); *A61B 8/4461* (2013.01); *A61B 2034/2063* (2016.02)

(58) Field of Classification Search
CPC ..... A61B 8/463; A61B 8/0841; A61B 8/4477; A61B 8/5207; A61B 8/14; A61B 8/4461; A61B 34/20; A61B 2034/2063
See application file for complete search history.

(56) References Cited

U.S. PATENT DOCUMENTS

2009/0247873 A1 10/2009 Kondo
2012/0099394 A1 4/2012 Choi et al.
(Continued)

FOREIGN PATENT DOCUMENTS

JP 2006-288580 A 10/2006
JP 2007-226 A 1/2007
(Continued)

OTHER PUBLICATIONS

International Preliminary Report on Patentability and Written Opinion of the International Searching Authority (forms PCT/IB/373 and PCT/ISA/237), dated Oct. 3, 2017, for International Application No. PCT/JP2016/058569, with an English translation of the Written Opinion.

(Continued)

*Primary Examiner* — Peter Luong
(74) *Attorney, Agent, or Firm* — Birch, Stewart, Kolasch & Birch, LLP

(57) ABSTRACT

There is provided an acoustic wave image generating apparatus and method capable of obtaining an image with good visibility of a needle. In a case where ultrasound waves having an intensity distribution centered on a first direction are transmitted to a subject, ultrasound echoes return from the subject. Ultrasound echo data indicating the ultrasound echoes are phased and added along lines in virtual reception directions. As the ultrasound transducers transmitting ultrasound waves are updated, a plurality of first ultrasound images are obtained. Since the ultrasound images having various angles can be obtained, an image with good visibility of a needle can be obtained in a case where the needle is inserted into the subject.

14 Claims, 35 Drawing Sheets

(51) Int. Cl.
*A61B 34/20* (2016.01)
*A61B 8/08* (2006.01)

(56) References Cited

U.S. PATENT DOCUMENTS

| | | |
|---|---|---|
| 2013/0274608 A1 | 10/2013 | Takeda et al. |
| 2014/0039316 A1 | 2/2014 | Ichioka et al. |
| 2015/0141831 A1* | 5/2015 | Yamamoto .......... G01S 7/52046 600/447 |
| 2015/0158387 A1 | 6/2015 | Satoh et al. |
| 2015/0223776 A1 | 8/2015 | Ohuchi et al. |
| 2016/0113624 A1 | 4/2016 | Katsuyama |

FOREIGN PATENT DOCUMENTS

| | | |
|---|---|---|
| JP | 2009-254780 A | 11/2009 |
| JP | 2012-105959 A | 6/2012 |
| JP | 2012-245092 A | 12/2012 |
| JP | 2013-192627 A | 9/2013 |
| JP | 2014-10056 A | 1/2014 |
| JP | 2014-30500 A | 2/2014 |
| JP | 2014-100556 A | 6/2014 |
| JP | 2015-27346 A | 2/2015 |
| WO | WO 2015/029499 A1 | 3/2015 |

OTHER PUBLICATIONS

International Search Report (form PCT/ISA/210), dated May 10, 2016, for International Application No. PCT/JP2016/058569, with an English translation.
English language European Search Report dated Apr. 5, 2018 and issued in co-pending European Application No. 16772350.1.
Chinese Office Action for Chinese Application No. 201680019458. 9, dated Sep. 4, 2019, with an English translation.

* cited by examiner

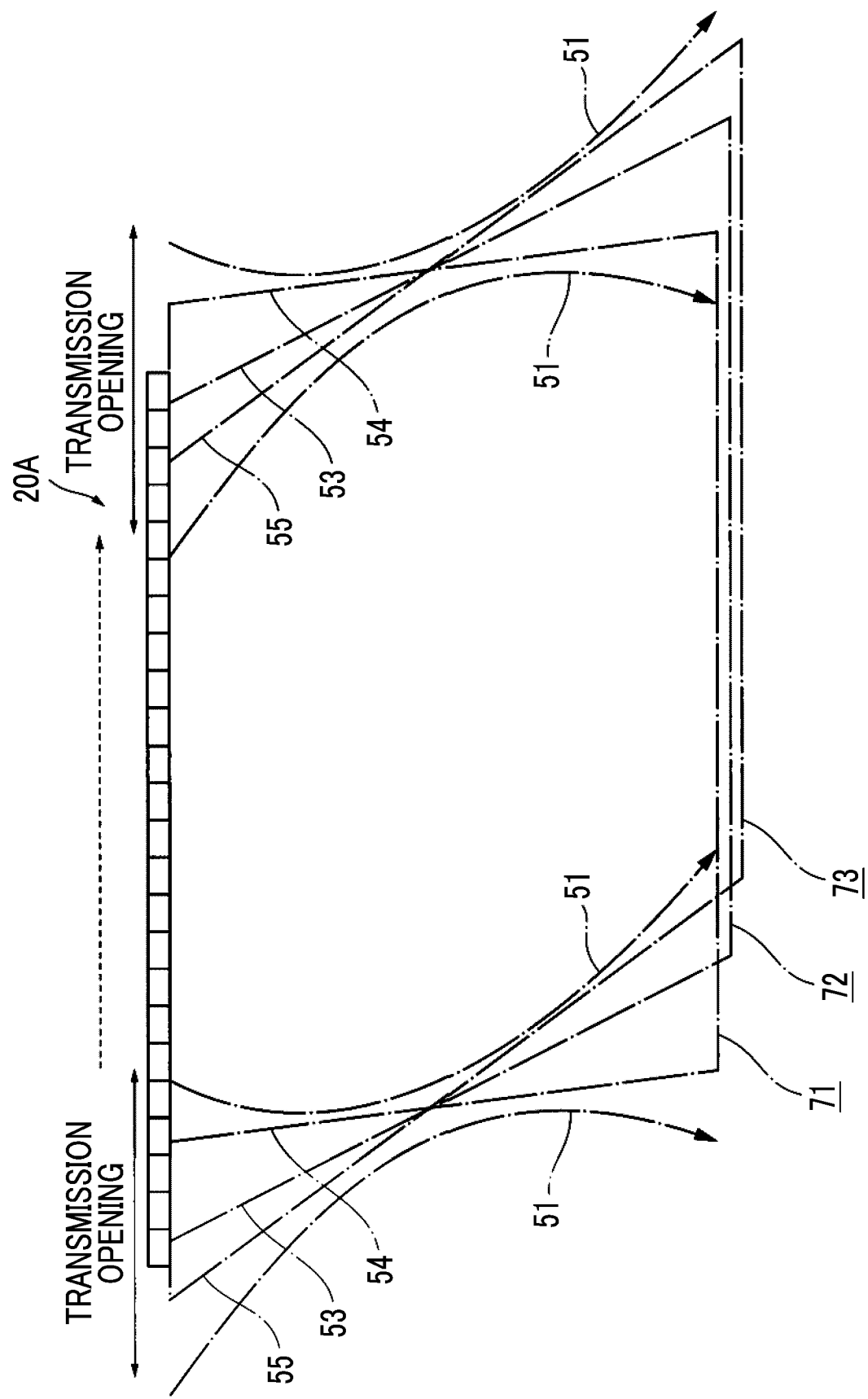

ACOUSTIC WAVE IMAGE GENERATING APPARATUS AND METHOD

CROSS-REFERENCE TO RELATED APPLICATIONS

This application is a Continuation of PCT International Application No. PCT/JP2016/058569 filed on Mar. 17, 2016, which claims priority under 35 U.S.C. § 119(a) to Japanese Patent Application No. 2015-076977 filed Apr. 3, 2015. Each of the above application(s) is hereby expressly incorporated by reference, in its entirety, into the present application.

BACKGROUND OF THE INVENTION

1. Field of the Invention

The present invention relates to an acoustic wave image generating apparatus and method.

2. Description of the Related Art

In anesthesia under ultrasound guidance using an ultrasound device for body surface or in aspiration biopsy cytology using an ultrasound endoscope, a procedure is performed while displaying an insertion needle on an ultrasound image. However, in a normal ultrasound image, there is a problem that the visibility of the needle with respect to the tissue is poor. The main cause of poor visibility is specular reflection of ultrasound waves on the needle surface. In the normal ultrasound image, the tissue is imaged by forming transmission/reception beams in the normal direction of the surface of the ultrasound probe. Therefore, since the reflected echo returns straight to the receiving opening from the structure parallel to the ultrasound probe, the sensitivity is maximized. However, in a case where the structure is inclined from the ultrasound probe, the ultrasound echo deviates from the receiving opening. Accordingly, the sensitivity is reduced. Since the insertion needle is generally inserted at an angle inclined by about 30° to 40° from the ultrasound probe surface, most of the ultrasound echoes deviate from the receiving opening. This makes it difficult to view the needle.

For this reason, apart from the imaging of the tissue, imaging (steer imaging) is performed by transmitting ultrasound waves deflected from the normal line of the ultrasound probe surface so as to be perpendicular to the needle, and a composite image of an image obtained as described above and a tissue image is displayed to greatly improve the visibility of the needle (JP2014-100556A). It is desirable that the ultrasound wave is perpendicular to the needle, and the user can manually select the angle. There are also a method of generating an image of an insertion needle from the phase information of a reception signal (JP2009-254780A), a method of acquiring a surface perpendicular to an insertion needle from the position information of the insertion needle and displaying an image of an insertion target and the needle (JP2007-226A), a method of generating an insertion image by image processing based on two pieces of ultrasound data and displaying the insertion image so as to overlap a tissue image (JP2014-10056A), and the like.

SUMMARY OF THE INVENTION

In practice, however, it is difficult to strictly match the insertion angle of the needle with the transmission angle of the ultrasound wave manually, and there is a problem that the visibility of the needle is lowered due to a small angle shift. In a case where the needle is lost, the user should perform fine adjustment of the angle or position of the ultrasound probe during the insertion. On the contrary, there is a possibility that the needle will be lost due to hand shake or movement of the patient.

It is an object of the present invention to obtain an image with good visibility of a needle.

An acoustic wave image generating apparatus according to the present invention comprises: an acoustic wave probe having a plurality of acoustic wave transducers that transmit acoustic waves to a subject, receive acoustic wave echoes from the subject, and output acoustic wave echo signals; a transmission control device (a transmission control device) for causing the acoustic wave transducers to transmit acoustic waves, which have an intensity distribution centered on a first direction from the plurality of acoustic wave transducers, while updating the plurality of acoustic wave transducers; an analog/digital conversion circuit that digitally converts a plurality of acoustic wave echo signals output from the plurality of acoustic wave transducers into first acoustic wave echo data; a virtual reception direction setting device (a virtual reception direction setting device) for setting a plurality of virtual reception directions; and a first acoustic wave image generation device (a first acoustic wave image generation device) for generating a plurality of first acoustic wave images by performing phasing addition of the first acoustic wave echo data, which is obtained by conversion in the analog/digital conversion circuit, along lines in the plurality of virtual reception directions.

The present invention also provides an acoustic wave image generating method. That is, in this method, a transmission control device causes acoustic wave transducers to transmit acoustic waves, which have an intensity distribution centered on a first direction from the plurality of acoustic wave transducers, while updating the plurality of acoustic wave transducers of an acoustic wave probe, which has the plurality of acoustic wave transducers that transmit acoustic waves to a subject, receive acoustic wave echoes from the subject, and output acoustic wave echo signals. An analog/digital conversion circuit digitally converts a plurality of acoustic wave echo signals output from the plurality of acoustic wave transducers into first acoustic wave echo data. A virtual reception direction setting device sets a plurality of virtual reception directions. A first acoustic wave image generation device generates a plurality of first acoustic wave images by performing phasing addition of the first acoustic wave echo data, which is obtained by conversion in the analog/digital conversion circuit, along lines in the plurality of virtual reception directions.

The acoustic wave image generating apparatus may further comprise a needle image generation device (a needle image generation device) for generating a needle image from the plurality of first acoustic wave images.

The needle image generation device may calculate an evaluation value of needle likeness for each of the plurality of first acoustic wave images and select a first acoustic wave image having a largest calculated evaluation value as the needle image.

The acoustic wave image generating apparatus may further comprise a first needle region detection device (a first needle region detection device) for detecting a region where a needle is present from each of the plurality of first acoustic wave images. In this case, for example, the needle image generation device calculates an evaluation value of needle likeness for the region detected by the first needle region detection device, and selects a first acoustic wave image having a largest calculated evaluation value as the needle image.

The needle image generation device may generate a new needle image using the plurality of first acoustic wave images.

The acoustic wave image generating apparatus may further comprise a coordinate transformation device (a coordinate transformation device) for aligning the plurality of first acoustic wave images by coordinate transformation.

The transmission control device may further cause the acoustic wave transducers to transmit acoustic waves, which have an intensity distribution centered on a second direction from the plurality of acoustic wave transducers, while updating the plurality of acoustic wave transducers. The analog/digital conversion circuit may digitally convert a plurality of acoustic wave echo signals, which are output from the plurality of acoustic wave transducers due to transmission of the acoustic waves having an intensity distribution centered on the second direction, into second acoustic wave echo data. The acoustic wave image generating apparatus may comprise a second acoustic wave image generation device (a second acoustic wave image generation device) for generating a second acoustic wave image by performing phasing addition of the second acoustic wave echo data along a line in the second direction and a first combining device (a first combining device) for combining the second acoustic wave image and the needle image.

For example, the transmission control device may cause acoustic waves to be transmitted in a state in which the number of acoustic wave transducers that transmit acoustic waves having an intensity distribution centered on the first direction is larger than the number of acoustic wave transducers that transmit acoustic waves having an intensity distribution centered on the second direction.

For example, the first combining device combines the needle image generated by the needle image generation device and the second acoustic wave image generated by the second acoustic wave image generation device with a predetermined weighting.

A line in the first direction may be included within a range determined by the lines in the plurality of virtual reception directions set by the virtual reception direction setting device.

One of the lines in the plurality of virtual reception directions set by the virtual reception direction setting device may match the line in the first direction.

The second direction is, for example, a direction perpendicular to each of the plurality of acoustic wave transducers, and the first direction is, for example, a direction inclined from a direction perpendicular to each of the plurality of acoustic wave transducers.

The first direction is, for example, a direction perpendicular to each of the plurality of acoustic wave transducers. The acoustic wave image generating apparatus may further comprise a second combining device (a second combining means) for combining a third acoustic wave image generated by phasing addition along a line in a direction perpendicular to each of the plurality of acoustic wave transducers, among the plurality of first acoustic wave images, and the needle image.

According to the present invention, acoustic waves having an intensity distribution centered on the first direction from the plurality of acoustic wave transducers of the acoustic wave probe are transmitted from the acoustic wave transducers. Then, the acoustic wave echo signals output from the acoustic wave transducers are digitally converted to obtain the first acoustic wave echo data. A plurality of virtual reception directions are set, and the first acoustic wave echo data is phased and added along the lines in the plurality of virtual reception directions, thereby generating a plurality of first acoustic wave images. Since a plurality of first acoustic wave images are generated by performing phasing addition of the first acoustic wave echo data along the lines in the plurality of virtual reception directions, various first acoustic wave images having different angles between the inserted needle and the virtual reception direction are obtained in the case of inserting the needle into the subject. The plurality of first acoustic wave images include a first acoustic wave image with good visibility of a needle.

BRIEF DESCRIPTION OF THE DRAWINGS

FIG. 13 shows how a plurality of first ultrasound images are generated.

DESCRIPTION OF THE PREFERRED EMBODIMENTS

In the present embodiment, an ultrasound wave is used as an acoustic wave. However, as long as an appropriate frequency is selected according to an object to be examined, measurement conditions, and the like, an acoustic wave having an audible frequency may be used without being limited to the ultrasound wave.

Figure 1:
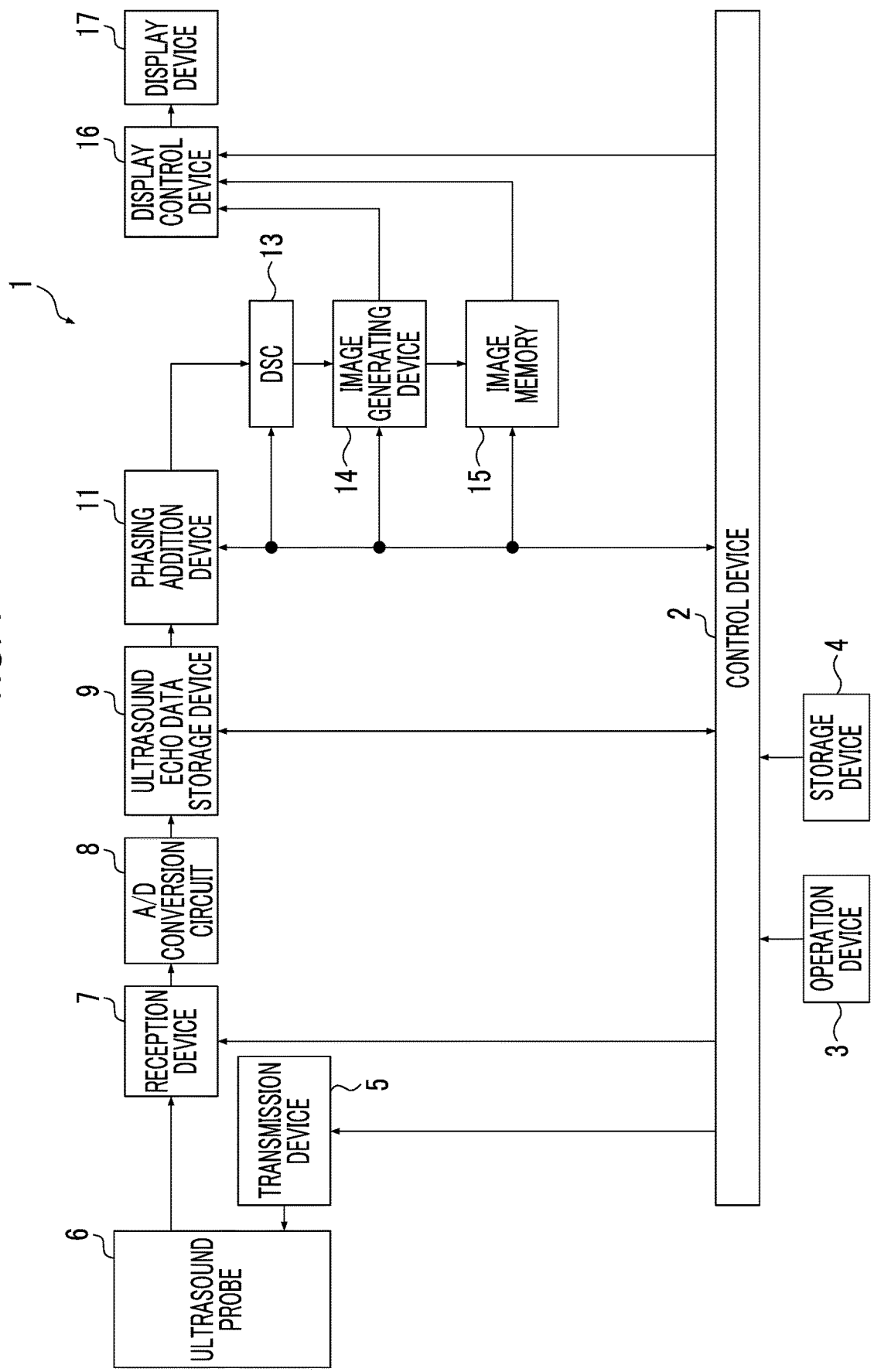
FIG. 1 is a block diagram showing the electrical configuration of an ultrasound diagnostic apparatus.

FIG. 1 shows an embodiment of the present invention, and is a block diagram showing the electrical configuration of an ultrasound diagnostic apparatus (acoustic wave image generating apparatus).

The overall operation of an ultrasound diagnostic apparatus 1 is controlled by a control device 2.

An operation device 3, which is operated by a doctor or the like who operates the ultrasound diagnostic apparatus 1, and a storage device 4, in which predetermined data and the like are stored, are connected to the control device 2.

An ultrasound probe 6 (acoustic wave probe) is included in the ultrasound diagnostic apparatus 1. The ultrasound probe 6 has a plurality of ultrasound transducers that transmit ultrasound waves (acoustic waves) to a subject, receive ultrasound echoes (acoustic wave echoes) from the subject, and output ultrasound echo signals (acoustic wave echo signals).

A control signal output from the control device 2 is supplied to a transmission device 5. Then, an electrical pulse is supplied to each ultrasound transducer of the ultrasound probe 6 from the transmission device 5. The electrical pulse is converted into an ultrasound wave by the ultrasound transducer, the ultrasound pulse propagates through the body of a subject, and the ultrasound echo returns to the ultrasound probe 6.

The ultrasound echo is converted into an electrical signal (ultrasound echo signal) by the ultrasound transducer.

Figure 2A:
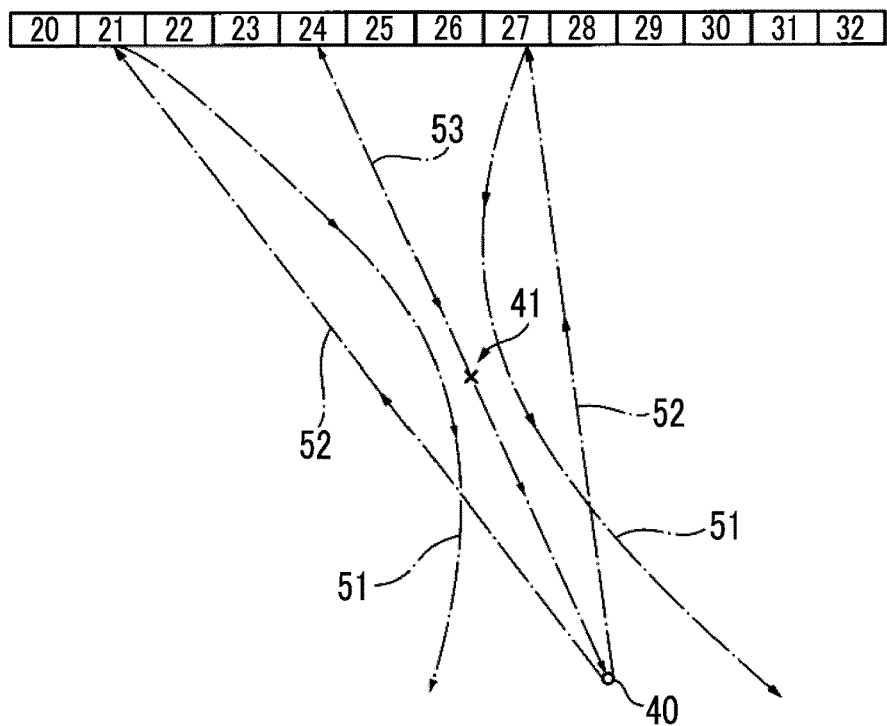
FIG. 2A shows how ultrasound waves are transmitted.

FIG. 2A shows a state in which ultrasound waves 51 are output from ultrasound transducers 21 to 27 among ultrasound transducers 20 to 32 included in the ultrasound probe 6.

It is assumed that the ultrasound waves 51 are transmitted from the ultrasound transducers 21 to 27. From the ultrasound transducers 21 to 27, the ultrasound waves 51 having an intensity distribution centered on a first direction from the ultrasound transducer 24, which is located at the center of the ultrasound transducers 21 to 27 transmitting the ultrasound waves 51, are transmitted by the transmission device 5 (a transmission control device). In the case shown in FIG. 2A, the first direction is a direction from the central ultrasound transducer 24 to a focusing position 41. The ultrasound waves 51 are transmitted from the ultrasound transducers 21 to 27 so as to be focused on the focusing position 41 on the line 53 in the first direction. Even if the ultrasound waves 51 are focused on the focusing position 41, the ultrasound waves 51 expand in a case where the ultrasound waves 51 exceed the focusing position 41.

When an observation target position 40 (a place where the medium changes in the subject) is present on the line 53 in the first direction, the ultrasound waves 51 are emitted to the observation target position 40, and ultrasound echoes 52 are generated from the observation target position 40. The ultrasound echoes 52 are received by the ultrasound transducers 21 to 27.

Figure 2B:
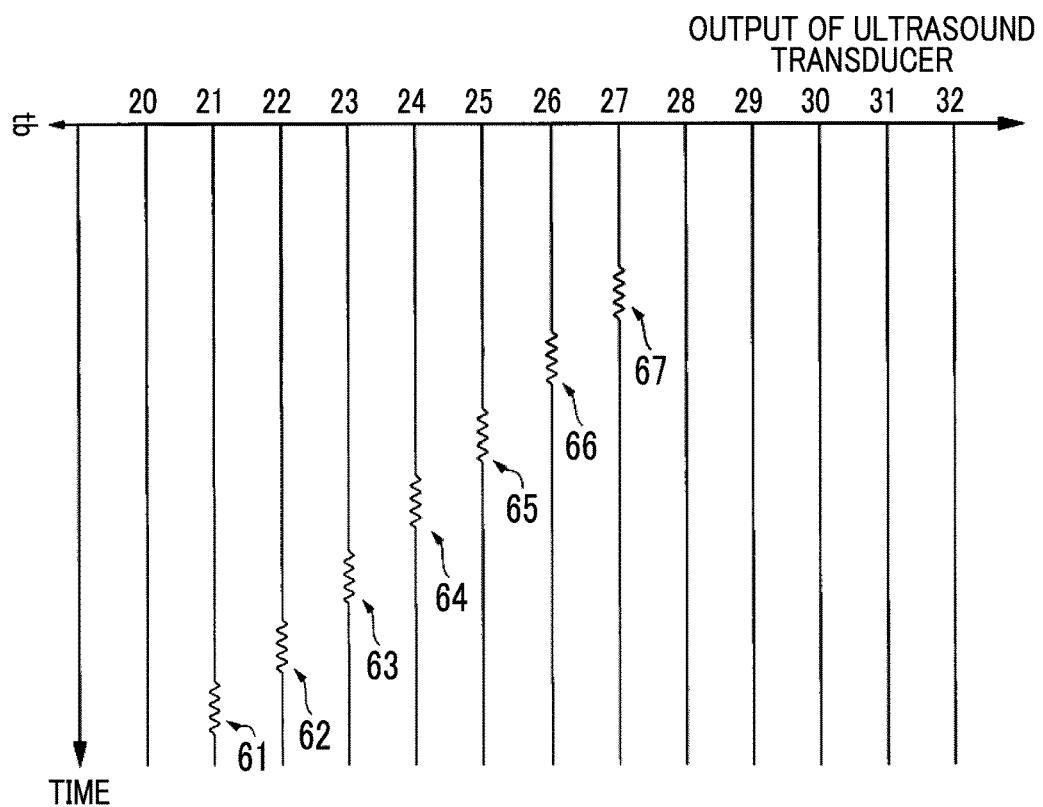
FIG. 2B is an example of an ultrasound echo signal.

FIG. 2B shows ultrasound echo signals 61 to 67 output from the ultrasound transducers 21 to 27 that have received the ultrasound echoes 52. The horizontal axis indicates the position of the ultrasound transducer, and the vertical axis indicates the elapsed time from time tb at which the ultrasound wave 51 is output from the ultrasound transducer.

Since a difference between the propagation distances of the ultrasound wave 51 and the ultrasound echo 52 occurs according to the positions of the ultrasound transducers 21 to 27, the output timings of the ultrasound echo signals 61 to 67 output from the ultrasound transducers 21 to 27 are also different for each ultrasound transducer. In the example shown in FIG. 2A, the propagation distances of the ultrasound waves 51 transmitted from the ultrasound transducers 21 to 27 and the propagation distances of the ultrasound echoes 52 from the observation target position 40 to the ultrasound transducers 21 to 27 are short in order of the ultrasound transducers 27, 26, 25, 24, 23, 22, and 21. For this reason, the ultrasound echo signal 67 is first output from the ultrasound transducer 27. After the output of the ultrasound echo signal 67 from the ultrasound transducer 27, the ultrasound echo signals 66, 65, 64, 63, 62, and 61 are output in order of the ultrasound transducers 26, 25, 24, 23, 22, and 21.

The output time difference of the ultrasound echo signals 66, 65, 64, 63, 62, and 61 is due to the positions of the ultrasound transducers 21 to 27. By performing addition (phasing addition) to the ultrasound echo signal 64 output from the ultrasound transducer 24 so that the ultrasound echo signals 66, 65, 64, 63, 62, and 61 are received only in the ultrasound transducer 24 by canceling the time difference, image data indicating a scanning line connecting the ultrasound transducer 24 and the observation target position 40 to each other (image data indicating one scanning line of the ultrasound image) is obtained. Thus, by performing phasing addition along the line in a virtual reception direction (virtual reception direction is a direction, from the observation target position 40, of the ultrasound transducer (in the case of FIG. 2A, the ultrasound transducer 24) in a case where it is assumed that an ultrasound echo is received in only one ultrasound transducer; in the case of FIG. 2A, a direction of the same line as the line 53 in the first direction is the virtual reception direction), image data indicating one scanning line of the ultrasound image is generated.

In order to perform the phasing addition, it is necessary to calculate the time difference. However, in the ultrasound transducers 21 to 27 that transmit the ultrasound wave 51, the transmission time of the ultrasound wave 51 is shifted according to the position so that the ultrasound waves are focused on the focusing position 41. Therefore, a total propagation distance of the propagation distance of the ultrasound wave 51 from the ultrasound transducer 24, which is located at the center of the ultrasound transducers 21 to 27 that transmit the ultrasound waves 51, to the observation target position 40 and a propagation distance from the observation target position 40 to each of the ultrasound transducers 21 to 27 is calculated, and the time difference is calculated from the difference in the total propagation distance.

Figure 3:
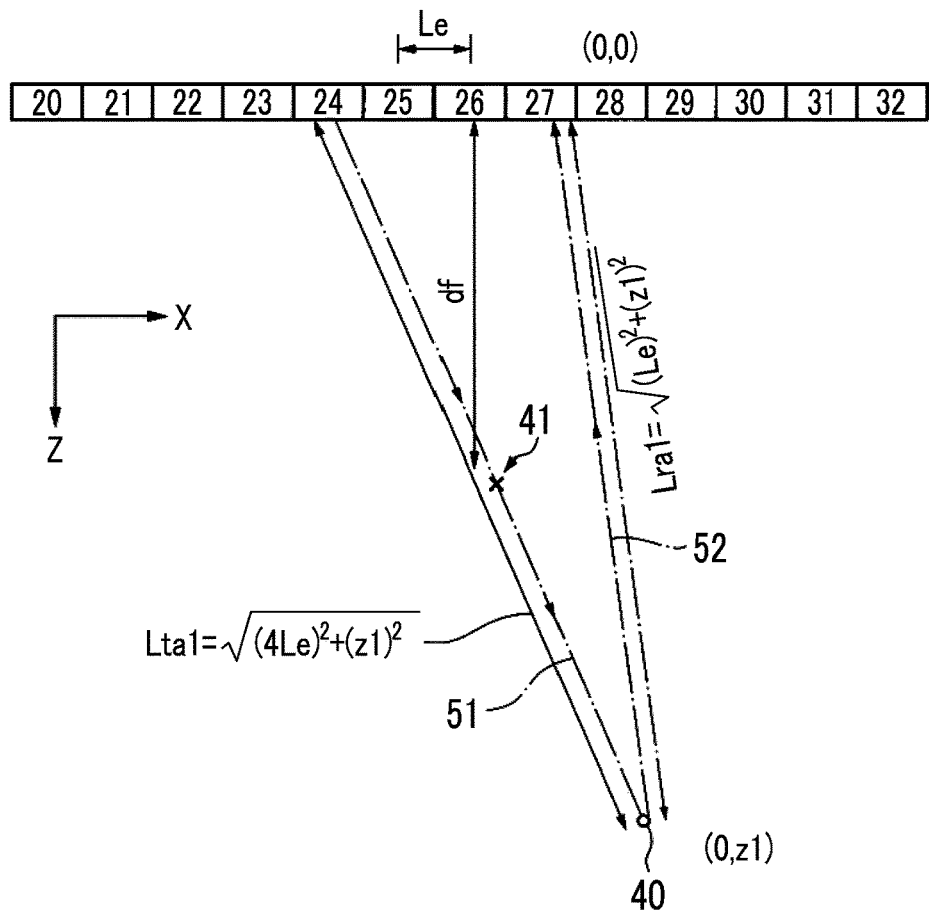
FIG. 3 shows the propagation distance of an ultrasound wave and the propagation distance of an ultrasound echo.

FIG. 3 shows an example of a method of calculating a total propagation distance of the propagation distance of the ultrasound wave 51 transmitted from the ultrasound transducer 24 and a propagation distance until the ultrasound echo 52 from the observation target position 40 is input to the ultrasound transducer 27 in a case where the observation target position 40 is located farther than the focusing position 41 as viewed from the ultrasound transducer 24.

One direction in which the ultrasound transducers 21 to 27 and the like are arranged is assumed to be an X direction, and a direction perpendicular to the one direction is assumed to be a Z direction. A distance between ultrasound transducers in the ultrasound transducers 20 to 32 and the like is defined as Le. It is assumed that the coordinates of the ultrasound transducer (in this case, the ultrasound transducer 28) closest to the observation target position 40 are (X, Z)=(0, 0), the coordinates of the focusing position 41 are (X, Z)=(-2Le, df), and the coordinates of the observation target position 40 are (X, Z)=(0, z1).

A propagation distance Lta1 until the ultrasound wave 51 transmitted from the ultrasound transducer 24 reaches the observation target position 40 through the focusing position 41 is $Lta1=\sqrt{(4Le)^2+(z1)^2}$. A propagation distance Lra1 until the ultrasound echo 52 reflected from the observation target position 40 returns from the observation target position 40 to the ultrasound transducer 27 is $Lra1=\sqrt{Le^2+(z1)^2}$. A propagation distance Lua1 obtained by adding up the propagation distance Lta1 of the ultrasound wave 51 and the propagation distance Lra1 of the ultrasound echo 52 is $Lua1=Lta1+Lra1=\sqrt{(4Le)^2+(z1)^2}+\sqrt{Le^2+(z1)^2}$. By dividing the propagation distance Lua1 obtained as described above by the speed of sound (speed of sound in the subject), the time from the transmission of the ultrasound wave 51 from the ultrasound transducer 24 to the reception of the ultrasound echo 52 in the ultrasound transducer 27 is obtained.

Similarly, the time from the transmission of the ultrasound wave 51 from the ultrasound transducer 24 to the reception of the ultrasound echo 52 in each of the ultrasound transducers 21, 22, 23, 24, 25, and 26 is obtained. From the time obtained as described above, the output time difference of the ultrasound echo signals 61 to 67 output from the ultrasound transducers 21 to 27 is calculated.

Figure 4:
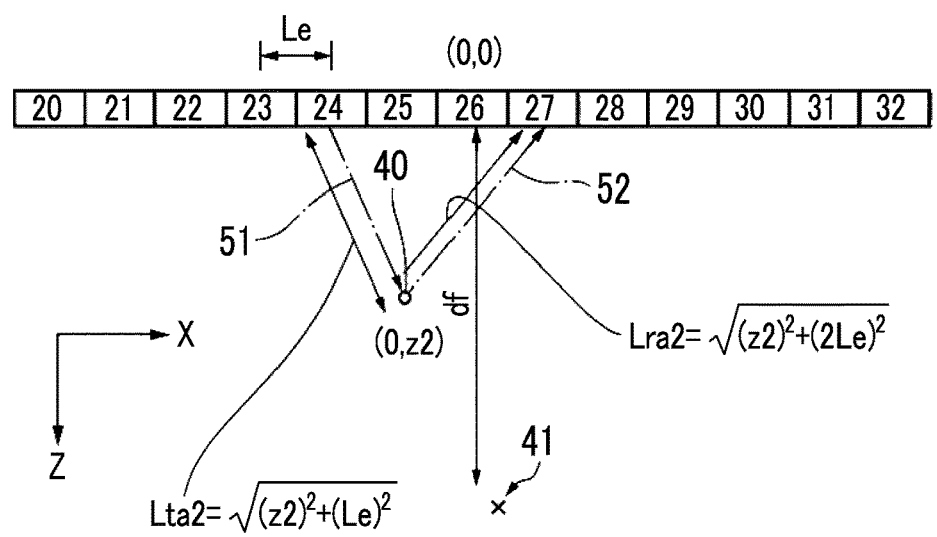
FIG. 4 shows the propagation distance of an ultrasound wave and the propagation distance of an ultrasound echo.

Unlike FIG. 3, FIG. 4 shows an example of a method of calculating a total propagation distance of the propagation distance of the ultrasound wave 51 transmitted from the ultrasound transducer 24 and a propagation distance until the ultrasound echo 52 from the observation target position 40 is input to the ultrasound transducer 27 in a case where the observation target position 40 is located closer than the focusing position 41 as viewed from the ultrasound transducer 24.

One direction in which the ultrasound transducers 21 to 27 and the like are arranged is assumed to be an X direction, and a direction perpendicular to the one direction is assumed to be a Z direction. A distance between ultrasound transducers in the ultrasound transducers 20 to 32 and the like is defined as Le. It is assumed that the coordinates of the ultrasound transducer (in this case, the ultrasound transducer 25) closest to the observation target position 40 are (X, Z)=(0, 0), the coordinates of the focusing position 41 are (X, Z)=(Le, df), and the coordinates of the observation target position 40 are (X, Z)=(0, z2).

A propagation distance Lta2 until the ultrasound wave 51 transmitted from the ultrasound transducer 24 reaches the observation target position 40 is $Lta2=\sqrt{(z2)^2+(Le)^2}$. A propagation distance Lra2 until the ultrasound echo 52 reflected from the observation target position 40 is input to the ultrasound transducer 27 from the observation target position 40 is $Lra2=\sqrt{(z2)^2+(2Le)^2}$. A propagation distance Lua2 obtained by adding up the propagation distance Lta2 of the ultrasound wave 51 and the propagation distance Lra2 of the ultrasound echo 52 is $Lua2=Lta2+Lra2=\sqrt{(Le)^2+(z2)^2}+\sqrt{(z2)^2+(2Le)^2}$. By dividing the propagation distance Lua2 obtained as described above by the speed of sound (speed of sound in the subject), the time from the transmission of the ultrasound wave 51 from the ultrasound transducer 24 to the reception of the ultrasound echo 52 in the ultrasound transducer 27 is obtained.

Similarly, the time from the transmission of the ultrasound wave 51 from the ultrasound transducer 24 to the reception of the ultrasound echo 52 in each of the ultrasound transducers 21, 22, 23, 24, 25, and 26 is obtained. From the time obtained as described above, the output time difference of the ultrasound echo signals 61 to 67 output from the ultrasound transducers 21 to 27 is calculated.

In FIGS. 3 and 4, the observation target position 40 is present in the transmission direction of the ultrasound transducer 24 located at the center of the ultrasound transducers 21 to 27 that transmit the ultrasound waves 51 (the ultrasound transducer 24, the focusing position 41, and the observation target position 40 are on the same line). However, the output time difference is similarly calculated even in a case where the observation target position 40 is not present in the transmission direction of the ultrasound transducer 24 located at the center of the ultrasound transducers 21 to 27 that transmit the ultrasound waves 51.

Referring back to FIG. 1, the ultrasound echo signals 61 to 67 output from the plurality of ultrasound transducers 21 to 27 are input to an A/D (analog/digital) conversion circuit 8 after being amplified in a receiving device 7. In the A/D conversion circuit 8, the plurality of ultrasound echo signals 61 to 67 output from the plurality of ultrasound transducers 21 to 27 are digitally converted into the first ultrasound echo data 61a to 67a. The first ultrasound echo data 61a to 67a is supplied to an ultrasound echo data storage device 9 so as to be temporarily stored therein.

The first ultrasound echo data 61a to 67a is read out from the first ultrasound echo data storage device 9, and the output time difference is corrected as follows in the phasing addition device 11.

Figure 5:
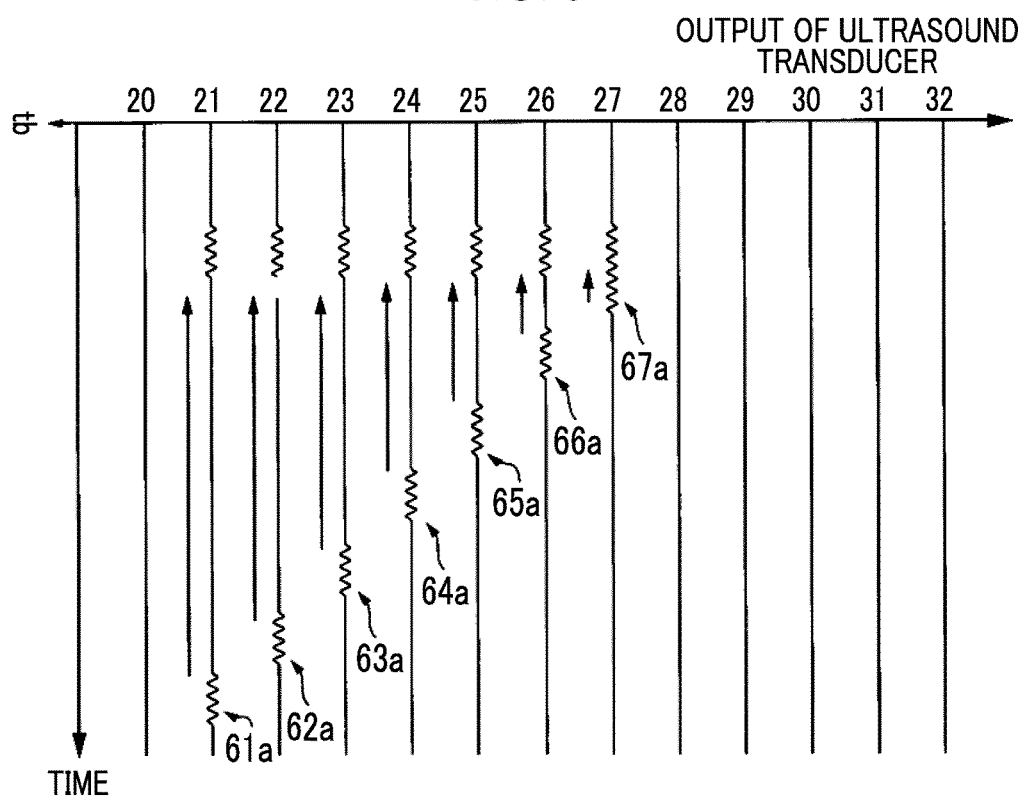
FIG. 5 shows the time difference correction of ultrasound echo data.

FIG. 5 shows how the output time difference of the first ultrasound echo data 61a to 67a is corrected.

After the output time difference of the first ultrasound echo data 61a to 67a is calculated, the output time of the first ultrasound echo data 61a to 67a is made to match the output time of the ultrasound echo data (in this case, ultrasound echo data 67a) that is output first among the pieces of first ultrasound echo data 61a to 67a.

Then, the first ultrasound echo data 61a to 67a after the output time correction is added as follows by the phasing addition device 11.

Figure 6:
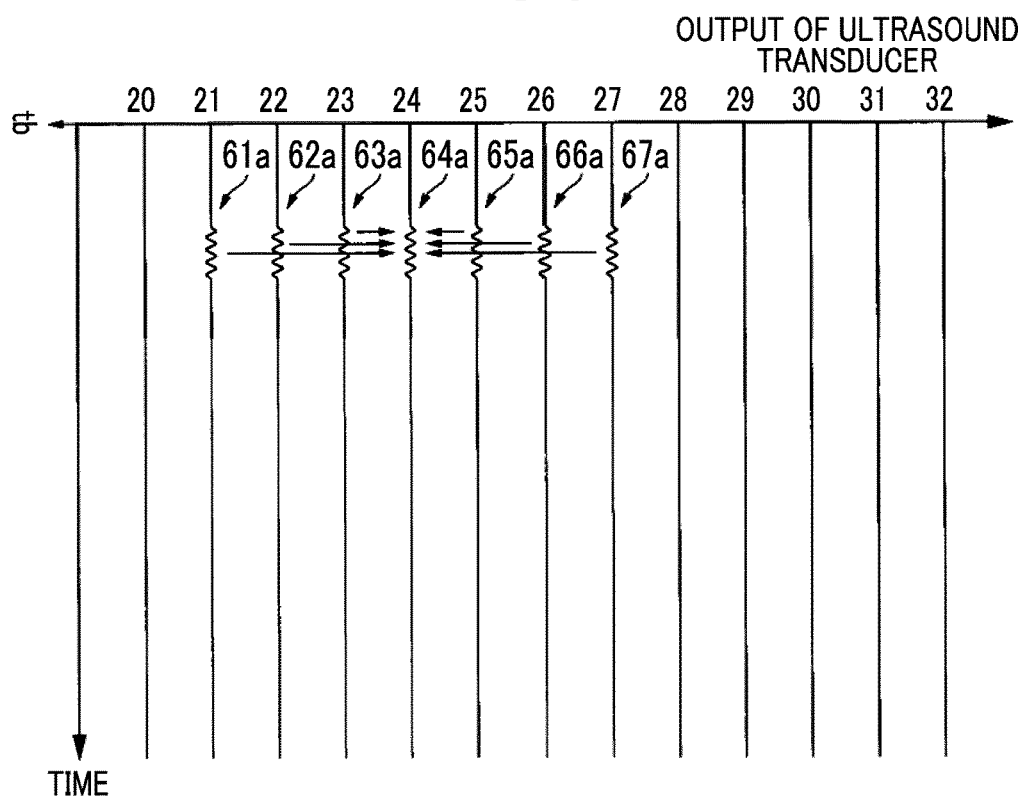
FIG. 6 shows the addition of ultrasound echo data.

FIG. 6 shows how the first ultrasound echo data 61a to 67a is added after the output time difference is corrected.

The first ultrasound echo data 61a to 67a whose output time difference has been corrected is added, so that the ultrasound echo signal 64 output from the ultrasound transducer 24 located at the center of the ultrasound transducers 21 to 27 is superimposed on digitally converted ultrasound echo data 64a. The output time correction and the addition of the first ultrasound echo data are the phasing addition in the phasing addition device 11. In this manner, phasing addition is performed along the line 53 in the first direction.

The first ultrasound echo data 61a to 67a after the phasing addition is input to a digital scan converter (DSC) 13. In the DSC 13, image data indicating the first ultrasound image of the line 53 in the first direction is generated. The direction of one line of the first ultrasound image is referred to as a virtual reception direction. In this case, the line 53 in the first direction and the line in the virtual reception direction are the same. However, the line 53 in the first direction and the line in the virtual reception direction may be different. The virtual reception direction is set by the operation device 3 (a virtual reception direction setting device).

Figure 7A:
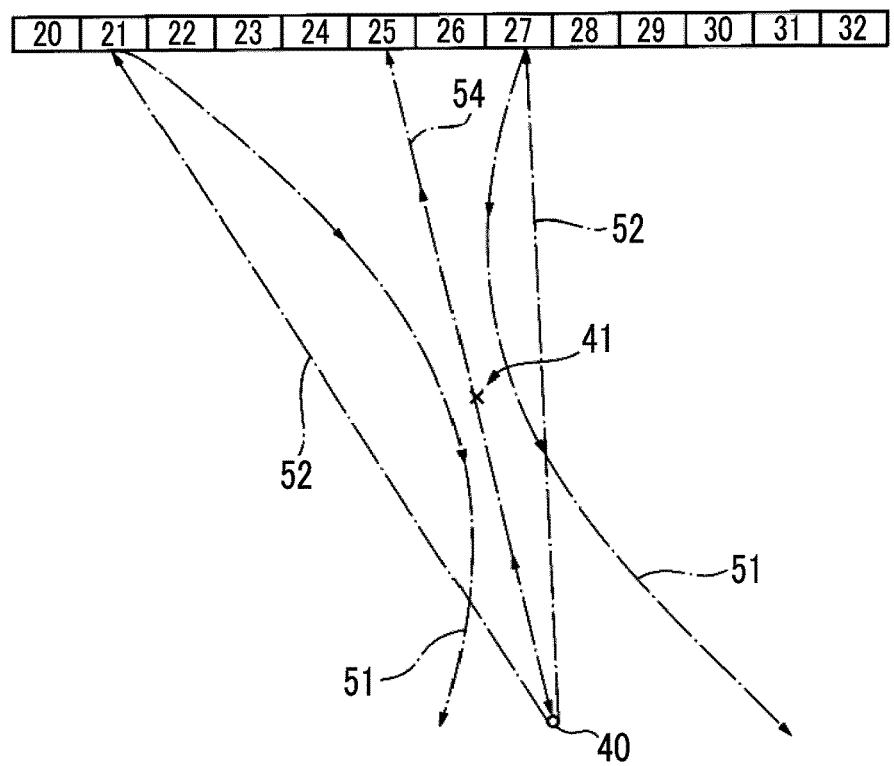
FIG. 7A shows how ultrasound waves are transmitted.

Referring to FIG. 7A, similarly to the case shown in FIG. 2A, in a case where the ultrasound waves 51 are transmitted from the ultrasound transducers 21 to 27, the ultrasound echo 52 is generated from the observation target position 40 and the ultrasound echo signals 61 to 67 are output from the ultrasound transducers 21 to 27 even in a case where the observation target position 40 is present at a position closest to the ultrasound transducer 27.

Figure 7B:
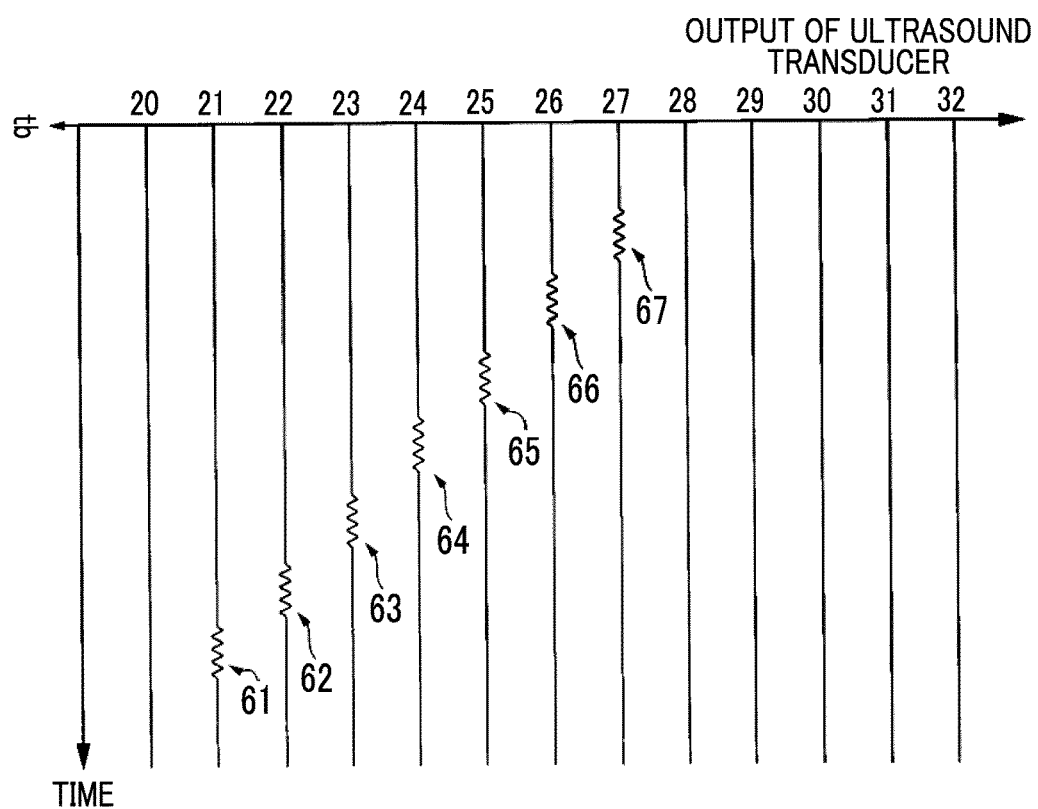
FIG. 7B is an example of an ultrasound echo signal.

FIG. 7B is an example of the ultrasound echo signals 61 to 67 output from the ultrasound transducers 21 to 27.

The output timings of the ultrasound echo signals 61 to 67 output from the ultrasound transducers 21 to 27 are different depending on the difference in the propagation distance between the ultrasound wave 51 and the ultrasound echo 52. The ultrasound echo signals 67, 66, 65, 64, 63, 62, and 61 are output in order of the ultrasound transducers 27, 26, 25, 24, 23, 22, and 21.

The ultrasound echo signals 61 to 67 are converted into first ultrasound echo data 61a to 67a by the A/D conversion circuit 8, and the first ultrasound echo data 61a to 67a is supplied to the ultrasound echo data storage device 9. The first ultrasound echo data 61a to 67a is read out from the ultrasound echo data storage device 9 and is supplied to the phasing addition device 11. In the phasing addition device 11, phasing addition is performed.

Figure 8:
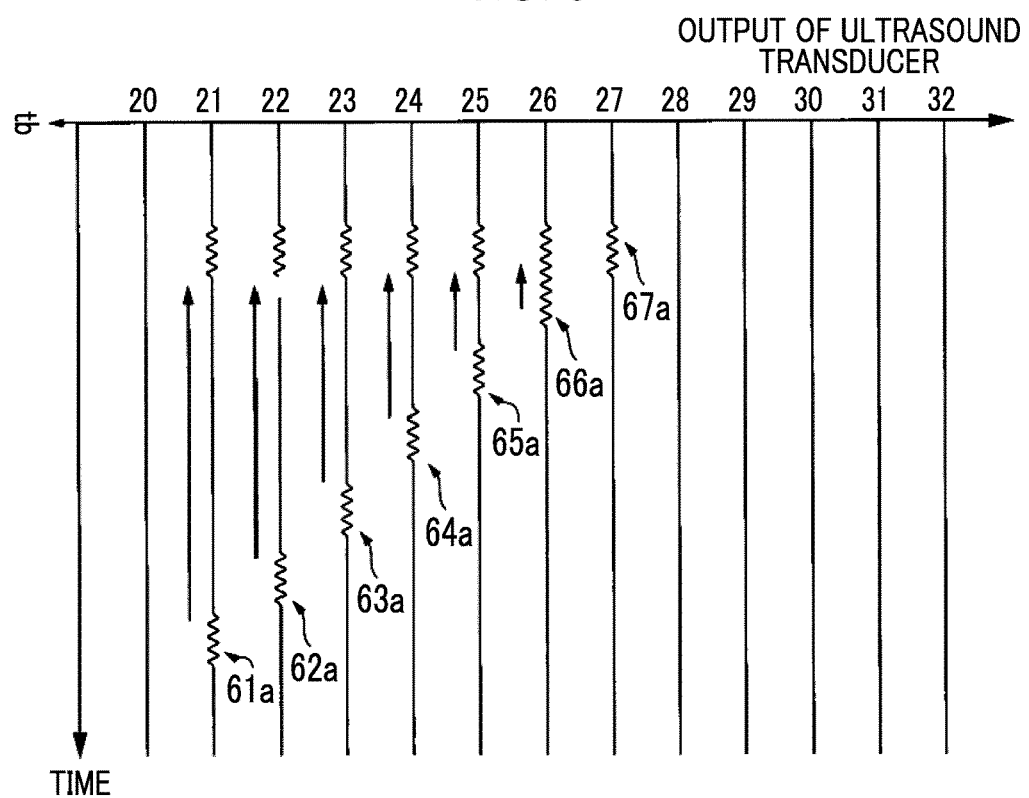
FIG. 8 shows the time difference correction of ultrasound echo data.

FIG. 8 shows how the output time of the first ultrasound echo data 61a to 67a is corrected.

In the phasing addition device 11, the output time of the first ultrasound echo data 61a to 67a is corrected so as to match the output timing of the ultrasound echo data 67a.

The first ultrasound echo data 61a to 67a after the output time correction is added as follows.

Figure 9:
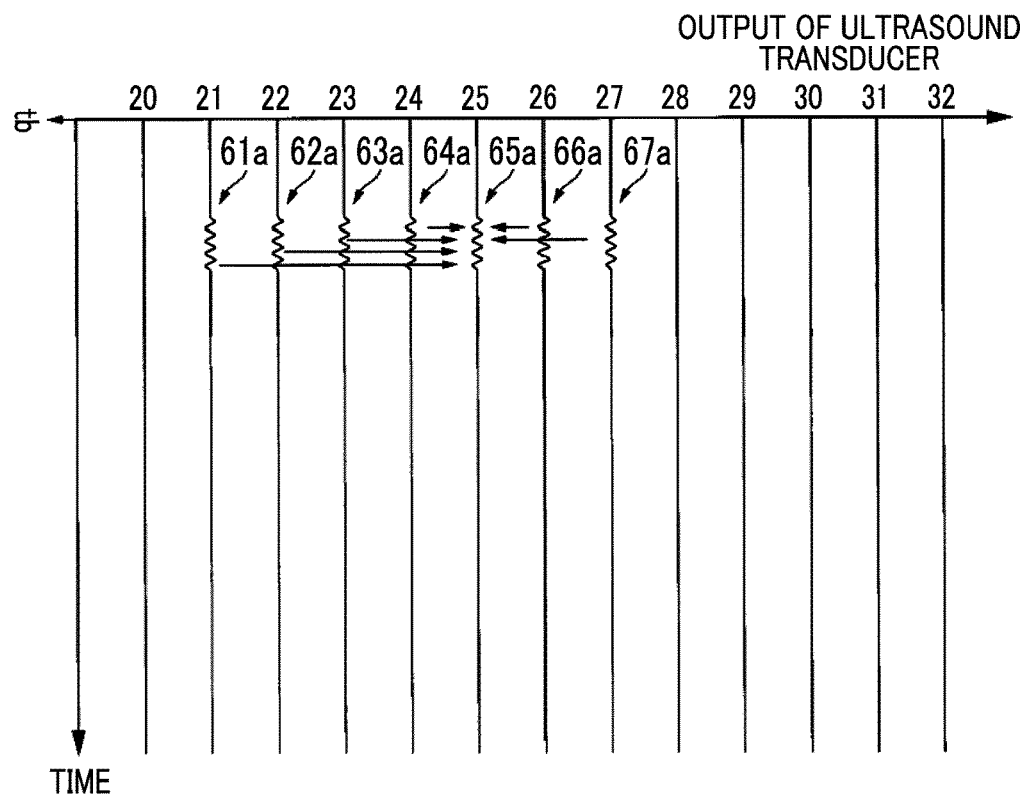
FIG. 9 shows phasing addition.

FIG. 9 shows how the first ultrasound echo data 61a to 67a is added.

In this case, the first ultrasound echo data 61a to 67a after the output time correction is added to superimpose on ultrasound echo data 65a obtained based on the ultrasound wave 51 from the ultrasound transducer 25. The first ultrasound echo data 61a to 67a is phased and added along a line 54 in the virtual reception direction.

The first ultrasound echo data 61a to 67a after the phasing addition is input to the DSC 13. In the DSC 13, image data indicating the first ultrasound image of the line 54 in the virtual reception direction in FIG. 7A is generated.

Figure 10A:
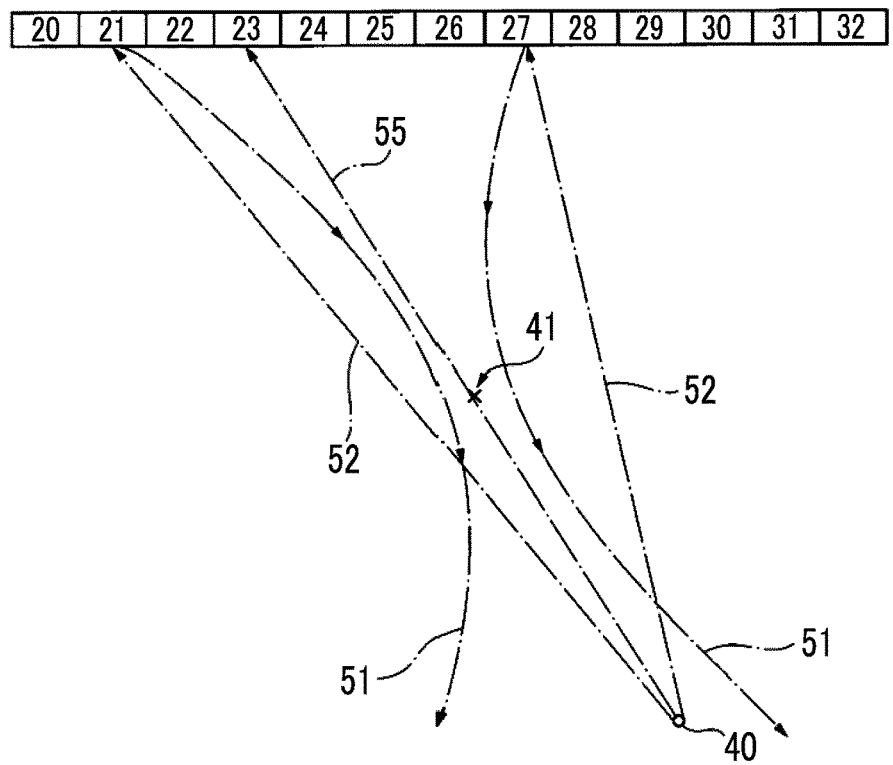
FIG. 10A shows how ultrasound waves are transmitted.

Referring to FIG. 10A, similarly to the case shown in FIG. 2A, in a case where the ultrasound waves 51 are transmitted from the ultrasound transducers 21 to 27, the ultrasound echo 52 is generated from the observation target position 40 and the ultrasound echo signals 61 to 67 are output from the ultrasound transducers 21 to 27 even in a case where the observation target position 40 is present at a position closest to the ultrasound transducer 29.

Figure 10B:
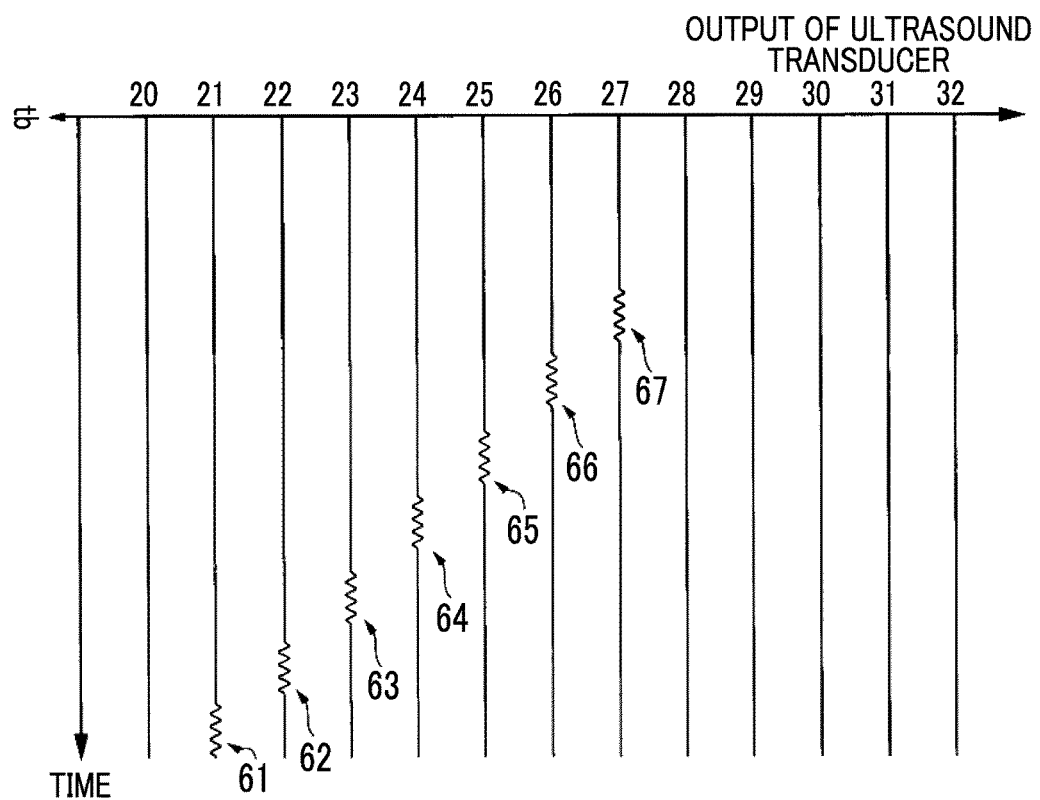
FIG. 10B is an example of an ultrasound echo signal.

FIG. 10B is an example of the ultrasound echo signals 61 to 67 output from the ultrasound transducers 21 to 27.

The output timings of the ultrasound echo signals 61 to 67 output from the ultrasound transducers 21 to 27 are different depending on the difference in the propagation distance between the ultrasound wave 51 and the ultrasound echo 52. The ultrasound echo signals 67, 66, 65, 64, 63, 62, and 61 are output in order of the ultrasound transducers 27, 26, 25, 24, 23, 22, and 21.

The ultrasound echo signals 61 to 67 are also converted into the first ultrasound echo data 61a to 67a by the A/D conversion circuit 8, and the first ultrasound echo data 61a to 67a is supplied to the ultrasound echo data storage device 9. The first ultrasound echo data 61a to 67a is read out from the ultrasound echo data storage device 9 and is supplied to the phasing addition device 11. In the phasing addition device 11, output time correction is performed.

Figure 11:
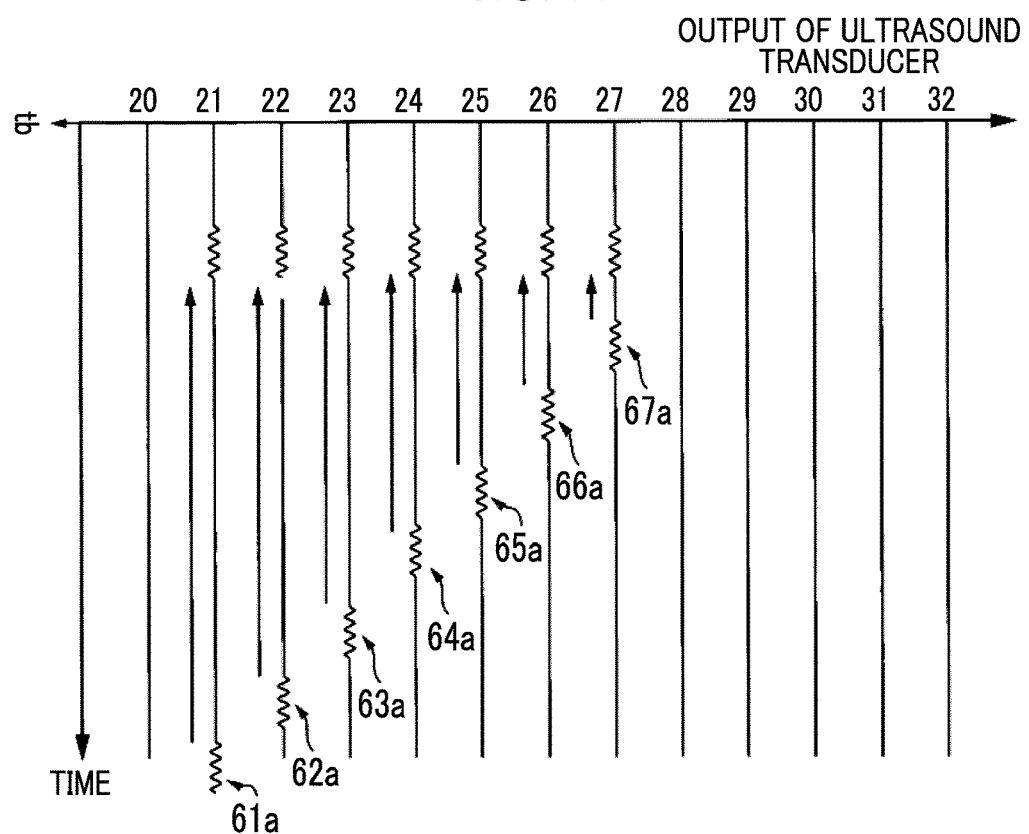
FIG. 11 shows the time difference correction of ultrasound echo data.

FIG. 11 shows how the output time of the ultrasound echo data 61a to 67a is corrected.

In the phasing addition device 11, the output time of the ultrasound echo data 61a to 67a is corrected so as to match the output timing of the ultrasound echo data 67a.

The first ultrasound echo data 61a to 67a after the output time correction is added by the phasing addition device 11.

Figure 12:
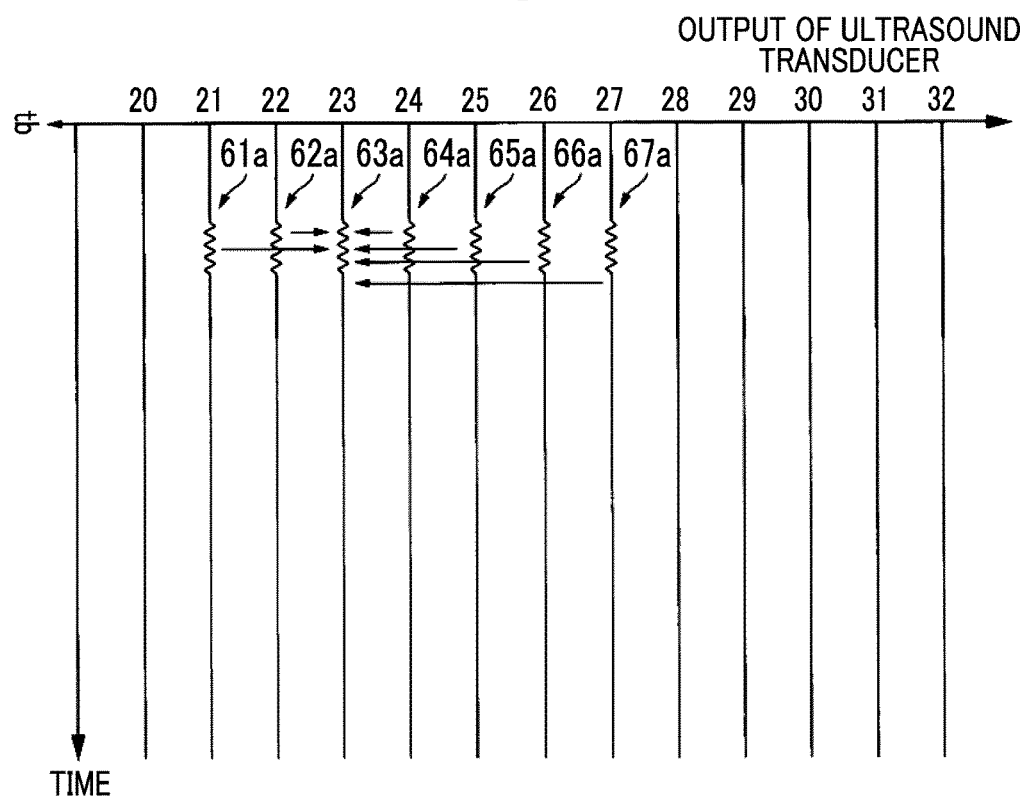
FIG. 12 shows phasing addition.

FIG. 12 shows how the first ultrasound echo data 61a to 67a is added.

In this case, the first ultrasound echo data 61a to 67a after the output time correction is added to superimpose on ultrasound echo data 63a obtained based on the ultrasound wave 51 from the ultrasound transducer 23 (phasing addition). The first ultrasound echo data 61a to 67a is phased and added along a line 55 in the virtual reception direction.

The first ultrasound echo data 61a to 67a after the phasing addition is input to the DSC 13. In the DSC 13, image data indicating the first ultrasound image of the line 55 in the virtual reception direction in FIG. 10A is generated.

FIG. 13 shows how a plurality of first ultrasound images are generated. In FIG. 13, the transmission opening has a size determined by the number of ultrasound transducers transmitting ultrasound waves at the same time, such as the ultrasound transducers 21 to 27.

Referring to FIG. 13, the processing described with reference to FIGS. 2A to 12 is repeated while updating an ultrasound transducer transmitting the ultrasound wave 51, in an ultrasound transducer group 20A including a plurality of ultrasound transducers, in one direction. Transmitting an ultrasound wave while updating an ultrasound transducer refers to transmitting an ultrasound wave while changing an ultrasound transducer transmitting an ultrasound wave.

Then, in the DSC 13, raster conversion into image data according to the scanning method of a normal television signal is performed, so that a plurality of first ultrasound images 71, 72, and 73, that is, a first ultrasound image 71 having the line 54 in the virtual reception direction, a first ultrasound image 72 having the line 53 in the virtual reception direction, and the first ultrasound image 73 having the line 55 in the virtual reception direction are generated. In this manner, a plurality of first ultrasound images 71, 72, and 73 are generated by phasing and adding the first ultrasound echo data 61*a* to 67*a* along the lines 53, 54, and 55 in a plurality of virtual reception directions.

Figure 14A:
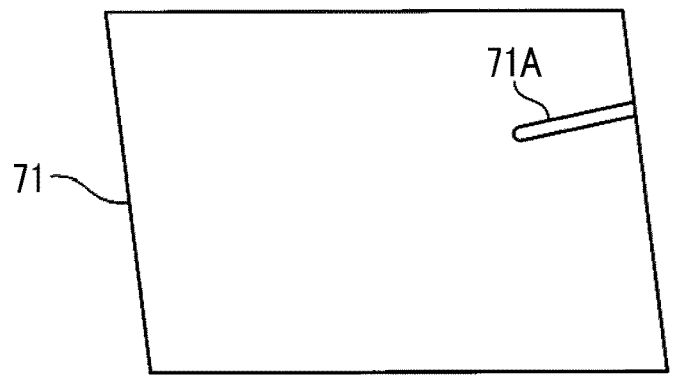
FIG. 14A shows an example of a first ultrasound image.
Figure 14B:
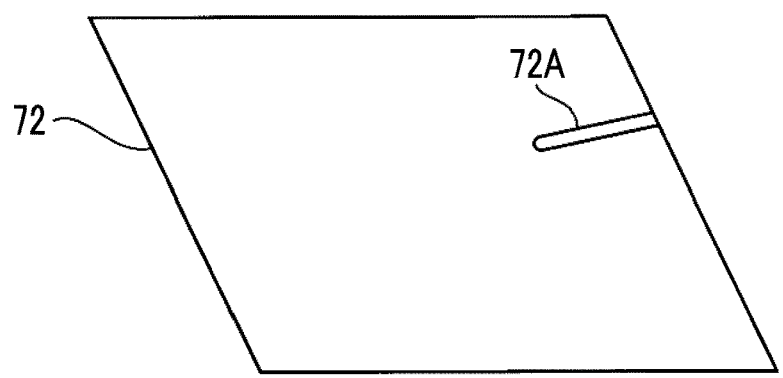
FIG. 14B shows an example of the first ultrasound image.
Figure 14C:
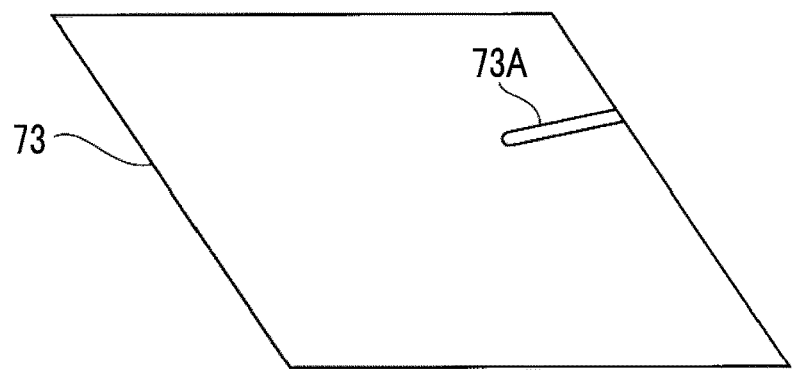
FIG. 14C shows an example of the first ultrasound image.

FIGS. 14A, 14B, and 14C are examples of a plurality of first ultrasound images 71, 72, and 73 obtained in a case where insertion into the subject is performed.

As shown in FIGS. 14A, 14B, and 14C, portions 71A, 72A, and 73A of the needle are reflected in the first ultrasound images 71, 72, and 73, respectively.

Since the first ultrasound images 71, 72, and 73 have different virtual reception directions, an angle at which the ultrasound echo 52 from the needle (in this case, each portion of the needle corresponds to the observation target position 40) is input to the ultrasound transducers 21 to 27 and the like is also different. Accordingly, the visibility of the portions 71A, 72A, and 73A of the needle is also different. In the present embodiment, a needle image that is easy to see can be obtained using the plurality of first ultrasound images 71, 72, and 73.

Figure 15:
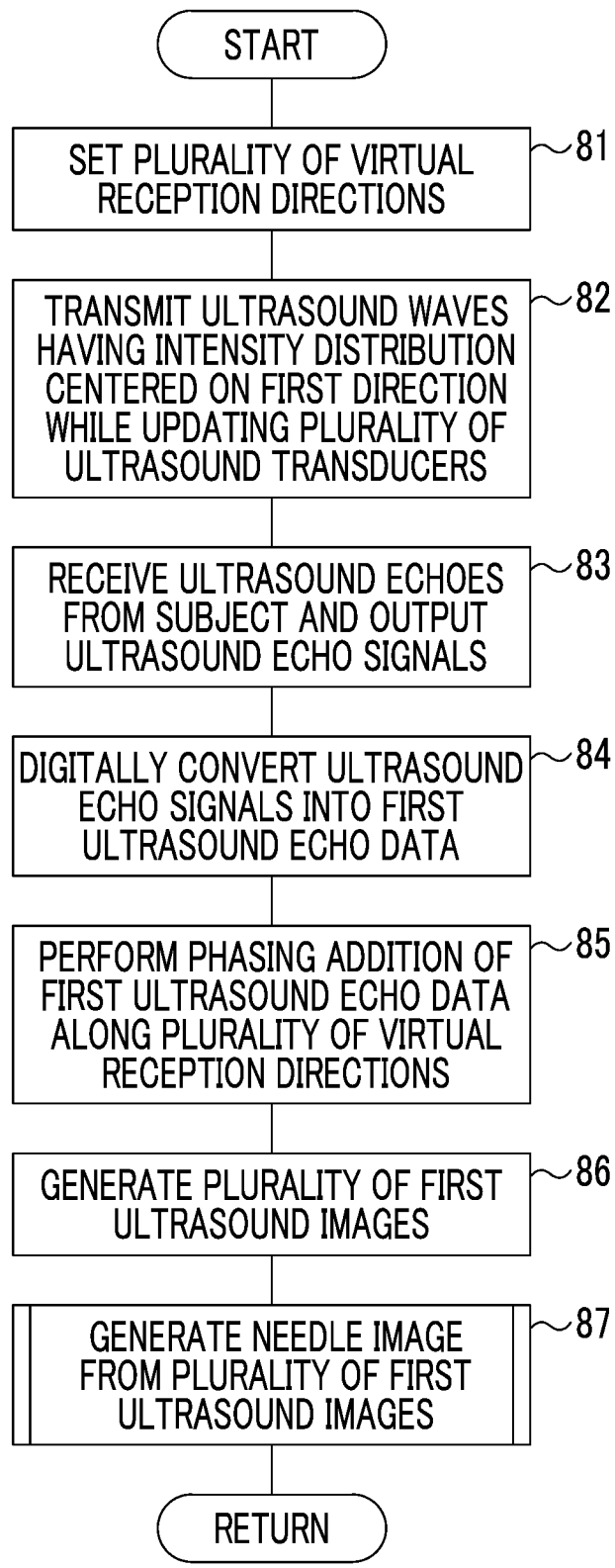
FIG. 15 is a flowchart showing the procedure of processing of the ultrasound diagnostic apparatus.

FIG. 15 is a flowchart showing the procedure of the processing of the ultrasound diagnostic apparatus 1.

A user, such as a doctor, sets a plurality of virtual reception directions using the operation device 3 (a virtual reception direction setting device) (step 81). The virtual reception directions are directions determined by the lines 53, 54, and 55. Then, while updating a plurality of ultrasound transducers transmitting the ultrasound waves 51, the ultrasound waves 51 having an intensity distribution centered on the line 54 in the first direction are transmitted from the ultrasound transducers 21 to 27 and the like by the transmission device 5 (a transmission control device) (step 82). The ultrasound echoes 52 from the subject are received by the ultrasound transducers 21 to 27 and the like, and ultrasound echo signals are output from the ultrasound transducers 21 to 27 and the like (step 83).

The plurality of ultrasound echo signals output from the plurality of ultrasound transducers 21 to 27 and the like are digitally converted into first ultrasound echo data by the A/D conversion circuit 8 (step 84). In the phasing addition device 11, phasing addition is performed along the lines 53, 54, and 55 in the plurality of virtual reception directions (step 85). The first ultrasound echo data after the phasing addition is input to the DSC 13, and a plurality of first ultrasound images 71, 72, and 73 are generated (step 86). The phasing addition device 11 and the DSC 13 serve as a first acoustic wave image generation device.

In a case where insertion into the subject is performed, a needle image is generated from a plurality of first ultrasound images generated as described above using the control device 2 (or an image generating device 14) (step 87) (a needle image generation device).

Figure 16:
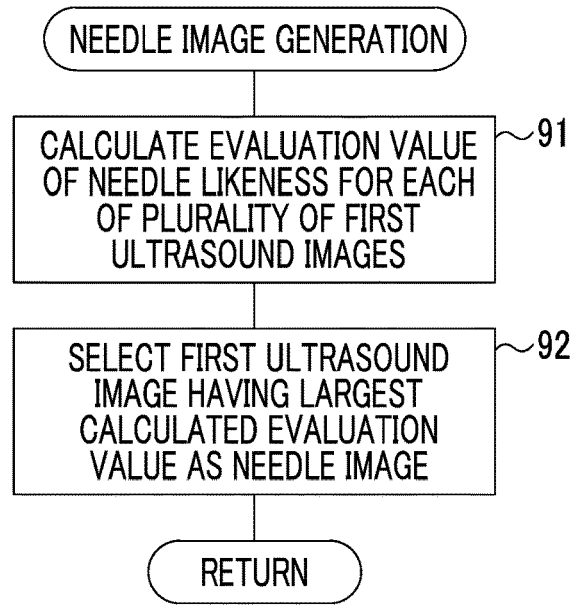
FIG. 16 is a flowchart showing the procedure of needle image generation processing.

FIG. 16 is a flowchart showing an example of processing for generating a needle image (processing of step 87 in FIG. 15).

In a case where regions of the portions 71A, 72A, and 73A of the needle are specified in the plurality of first ultrasound images 71, 72, and 73, an evaluation value of the needle likeness of the insertion needle in each region is calculated by the control device 2 (step 91). Information regarding the needle (thickness, material, and the like of the needle) is stored in the storage device 4, and the evaluation value of the needle likeness is calculated by referring to the information regarding the insertion needle stored in the storage device 4. For example, the evaluation value of the needle likeness is calculated based on whether or not the needle has a thickness close to the thickness of the needle stored in the storage device 4 or whether or not the needle has linearity. A first ultrasound image including a needle image having the largest evaluation value, among the calculated evaluation values of the needle likeness, is selected as a needle image by the control device 2 (a needle image generation device) (step 92). For example, in a case where it is determined that the evaluation value of the needle likeness of the portion 72A of the needle shown in FIG. 14B is the largest, the first ultrasound image 72 is selected as a needle image.

Figure 17:
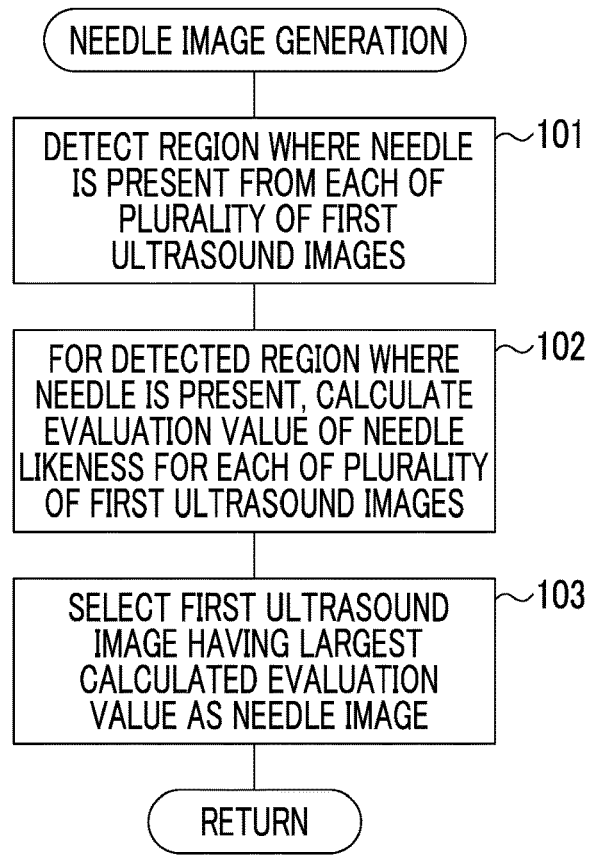
FIG. 17 is a flowchart showing the procedure of needle image generation processing.

FIG. 17 is a flowchart showing another example of the processing for generating a needle image (processing of step 87 in FIG. 15).

Processing for detecting a needle region where the portions 71A, 72A, and 73A of the needle are present from each of the plurality of first ultrasound images 71, 72, and 73 is performed (step 101). Specifically, information regarding the needle, such as the thickness and the material of the insertion needle, is stored in the storage device 4. Using the information regarding the needle, feature points of the needle are extracted from the generated first ultrasound images 71, 72, and 73. For example, constant false alarm rate (CFAR) processing or the like is performed by applying an edge extraction filter, edge image data is generated by performing threshold value processing, and candidate points of the needle are extracted as feature points from the edge image data. Since the surface of the needle is smooth, scattering of ultrasound waves is unlikely to occur. For this reason, in the first ultrasound images 71, 72, and 73, the needle is discontinuously displayed. Therefore, by performing threshold value processing on the first ultrasound images 71, 72, and 73 in which the needle is present, it is possible to extract points indicating a part of the needle that is discontinuous. Based on the distribution of the extracted needle candidate points, a line segment or a straight line (needle candidate line) showing the needle and the extension line of the needle is generated. A region including the generated needle candidate line is specified as a region where the needle is present by the control device 2. Thus, a region where the needle is present is detected from each of the plurality of first ultrasound images 71, 72, and 73 by the control device 2 (a first needle region detection device) (step 101).

For the region where the needle is present that has been detected as described above, an evaluation value of the needle likeness is calculated by the control device 2 (a needle likeness evaluation value calculation device) for each of the plurality of first ultrasound images 71, 72, and 73 (step 102). A first ultrasound image having the largest calculated evaluation value among the first ultrasound images 71, 72, and 73 is selected as a needle image by the control device 2 (a needle image selection device) (step 103).

Figure 18:
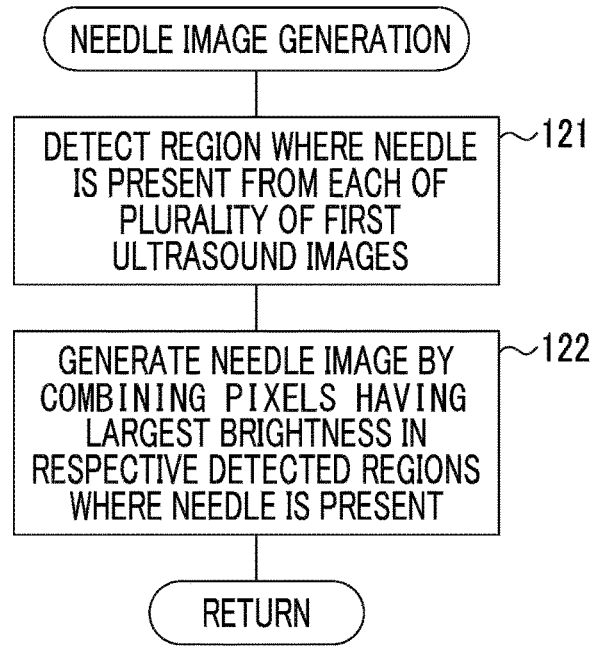
FIG. 18 is a flowchart showing the procedure of needle image generation processing.

FIG. 18 is a flowchart showing an example of specific processing for generating a new needle image (processing of step 87 in FIG. 15).

A region where the needle is present is detected from each of the plurality of first ultrasound images 71, 72, and 73 (step 121). Pixels with the maximum brightness in the respective detected regions where the needle is present are combined by the image generating device 14 to generate a new needle image (step 122).

Figure 19:
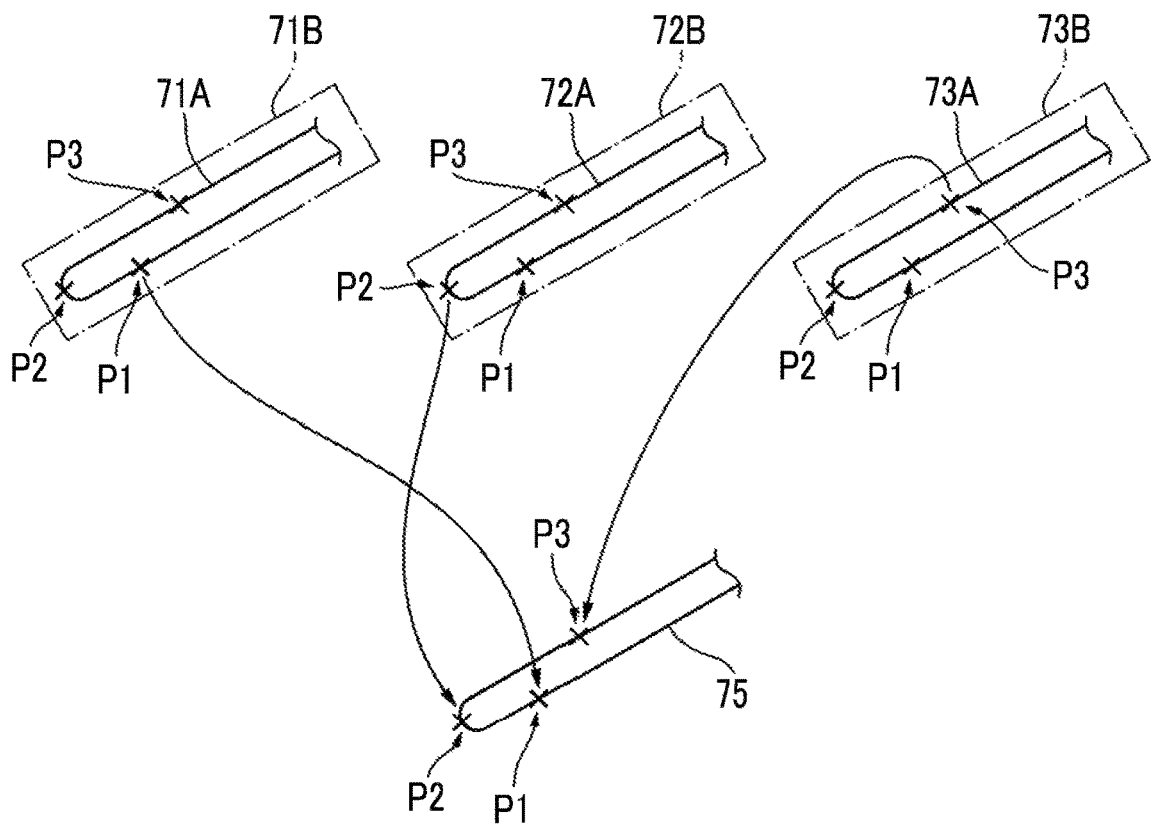
FIG. 19 shows how needle images are combined.

FIG. 19 shows how a new needle image is generated.

It is assumed that regions 71B, 72B, and 73B where the needle is present are detected from the first ultrasound images 71, 72, and 73, respectively. In the control device 2, the regions 71B, 72B, and 73B where the needle is present are coordinate-transformed so that the same parts match each other. Therefore, it is assumed that the coordinate positions of pixels P1, P2, and P3 in each of the regions 71B, 72B, and 73B where the needle is present correspond to each other in the regions 71B, 72B, and 73B where the needle is present. For example, for the brightness of a portion indicated by the pixel P1, assuming that the brightness of a portion indicated by the pixel P1 in the region 71B where the needle is present is the largest, a needle image 75 is generated by combination using the pixel P1 in the region 71B where the needle is present. Similarly, assuming that the brightness of a portion indicated by the pixel P2 is the largest, the needle image 75 is generated by combination using the pixel P2 in the region 72B where the needle is present. Assuming that the brightness of a portion indicated by the pixel P3 is the largest, the needle image 75 is generated by combination using the pixel P3 in a region 73B where the needle is present. The same applies to other pixels. For pixels showing the same portion, the needle image 75 is generated by the image generating device 14 using a pixel with the highest brightness.

For the pixels showing the same portion, the needle image 75 is generated by combination using a pixel with the highest brightness among the regions 71B, 72B, and 73B in which the needle is present. However, the needle image 75 may be generated using a pixel with the intermediate brightness of the brightnesses of three pixels showing the same portion among the regions 71B, 72B, and 73B where the needle is present. Alternatively, the needle image 75 may be generated using an average value of three pixels showing the same portion among the regions 71B, 72B, and 73B where the needle is present.

Figure 20:
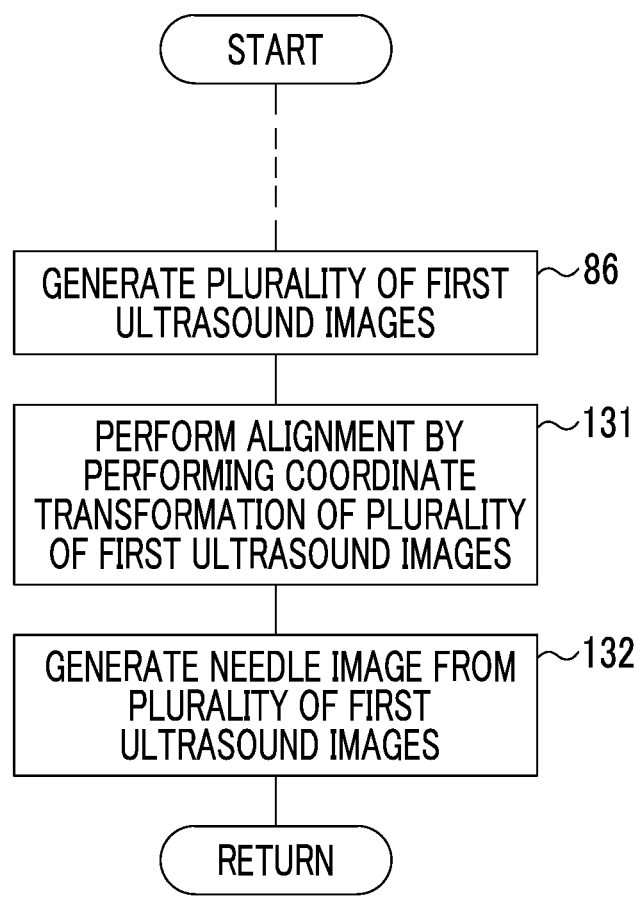
FIG. 20 is a flowchart showing the procedure of the processing of the ultrasound diagnostic apparatus.

FIG. 20 is a flowchart showing a part of the procedure of the processing of the ultrasound diagnostic apparatus 1. The flowchart shown in FIG. 20 corresponds to the flowchart shown in FIG. 15, and the processing of steps 81 to 85 in FIG. 15 is omitted in FIG. 20. The processing of step 86 shown in FIG. 20 is performed subsequent to the processing of steps 81 to 85 in FIG. 15.

By performing the processing of steps 81 to 85 shown in FIG. 15, a plurality of first ultrasound images 71, 72, and 73 are generated (step 86). The plurality of generated first ultrasound images 71, 72, and 73 are coordinate-transformed by the control device 2 (a coordinate transformation device), thereby being aligned so as to have the same shape (step 131). The alignment may be performed so that some of the plurality of first ultrasound images 71, 72, and 73 have the same shape, or may be performed so that all of the plurality of first ultrasound images 71, 72, and 73 have the same rectangular shape. A needle image is generated from the plurality of aligned first ultrasound images 71, 72, and 73 (step 132). Due to the alignment, the evaluation value is calculated with the same shape in the case of calculating the evaluation value of the needle likeness. Therefore, a more accurate calculation is possible. In addition, the needle image can be generated more accurately.

Figure 21:
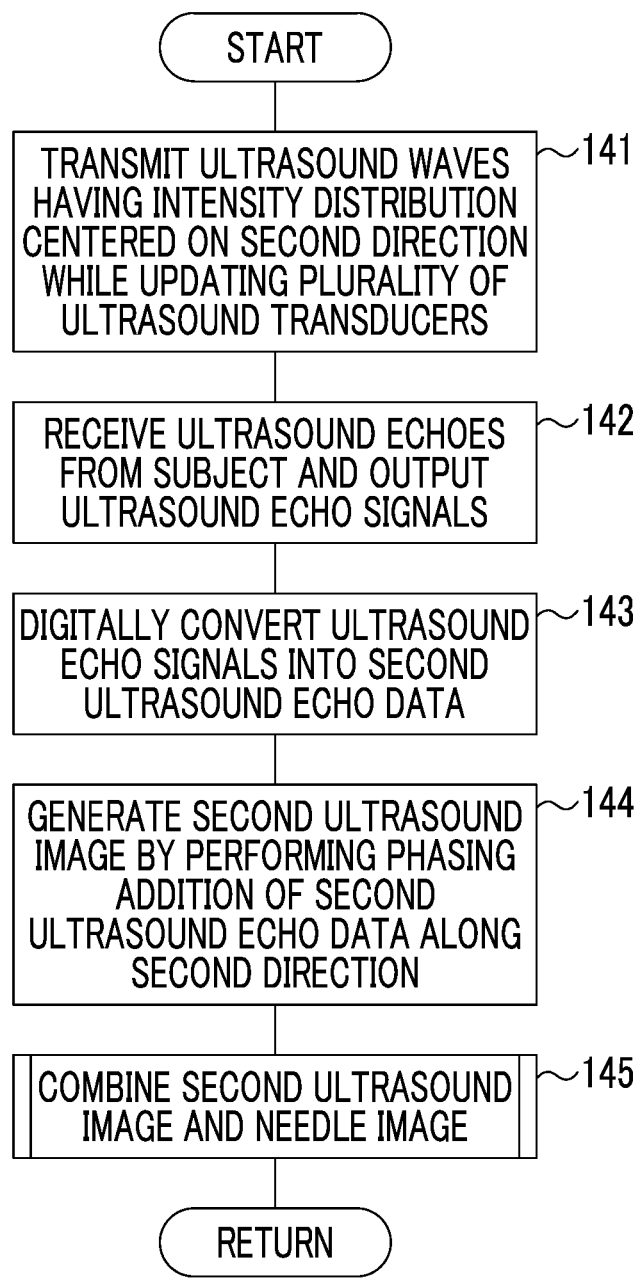
FIG. 21 is a flowchart showing the procedure of processing for generating a second ultrasound image.

FIG. 21 is a flowchart showing the procedure of the processing of the ultrasound diagnostic apparatus 1. The procedure of the processing shown in FIG. 21 is for generating a second ultrasound image. Although the plurality of first ultrasound images 71 to 73 are mainly for obtaining a needle image, the second ultrasound image is for obtaining an image of the tissue inside the subject.

By the transmission device 5 (a transmission control device), ultrasound waves having an intensity distribution centered on the second direction are transmitted from the ultrasound transducers while updating the plurality of ultrasound transducers (step 141). Ultrasound echoes from the subject are received by the ultrasound transducers, and ultrasound echo signals are output from the ultrasound transducers (step 142). The ultrasound echo signals are digitally converted into second ultrasound echo data by the A/D conversion circuit 8 (step 143).

The second ultrasound echo data is phased and added along a line in the second direction by the phasing addition device 11. The ultrasound echo data after the phasing addition is input to the DSC 13, and a second ultrasound image is generated by the DSC 13 (step 144). The phasing addition device 11 and the DSC 13 serve as a second ultrasound image generation device. After generating the second ultrasound image as described above, the generated second ultrasound image and the generated needle image are combined by the image generating device 14 (a first combining device) (step 145).

Figure 22:
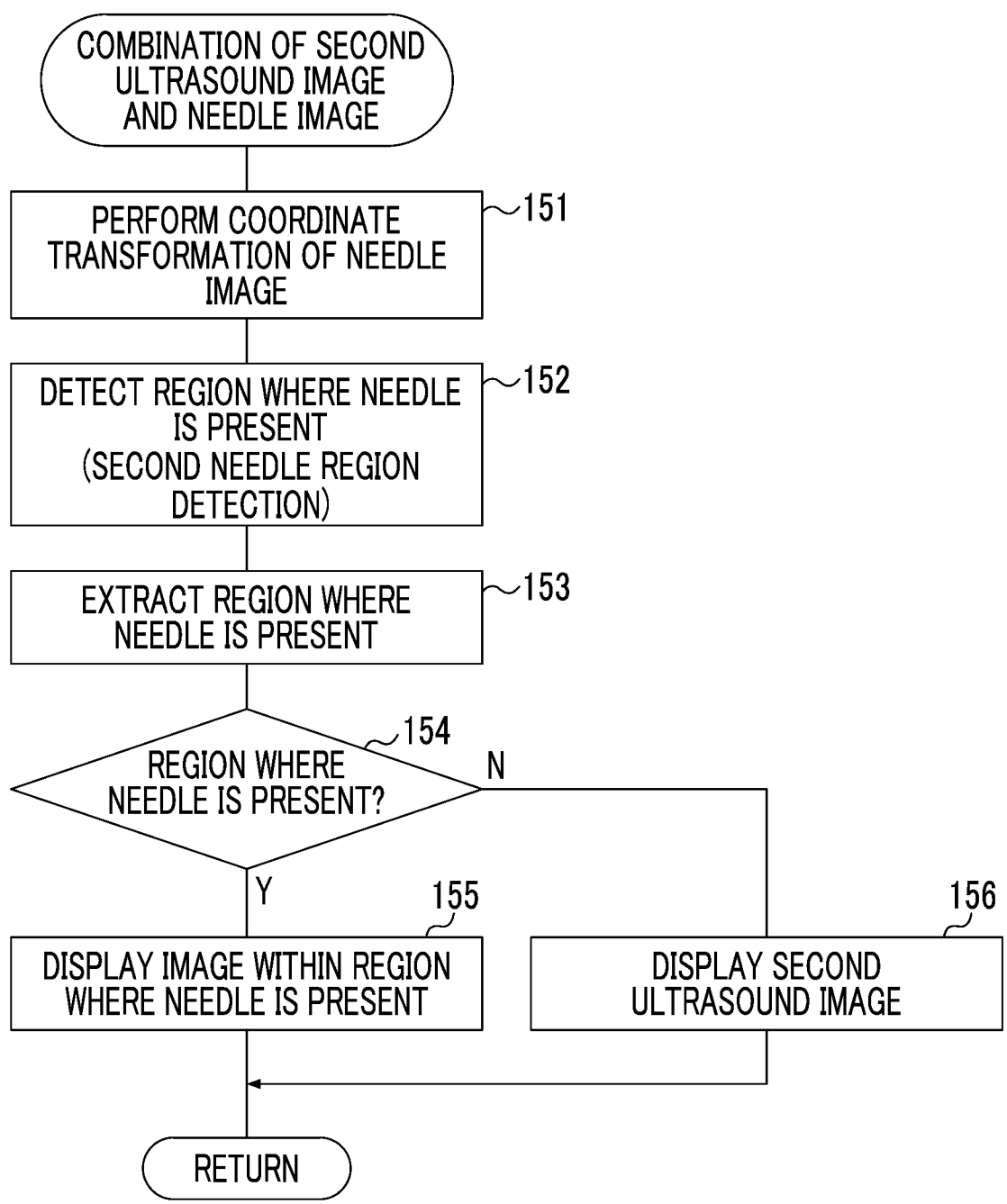
FIG. 22 is a flowchart showing the procedure of processing for combining a second ultrasound image and a needle image.
Figure 23:
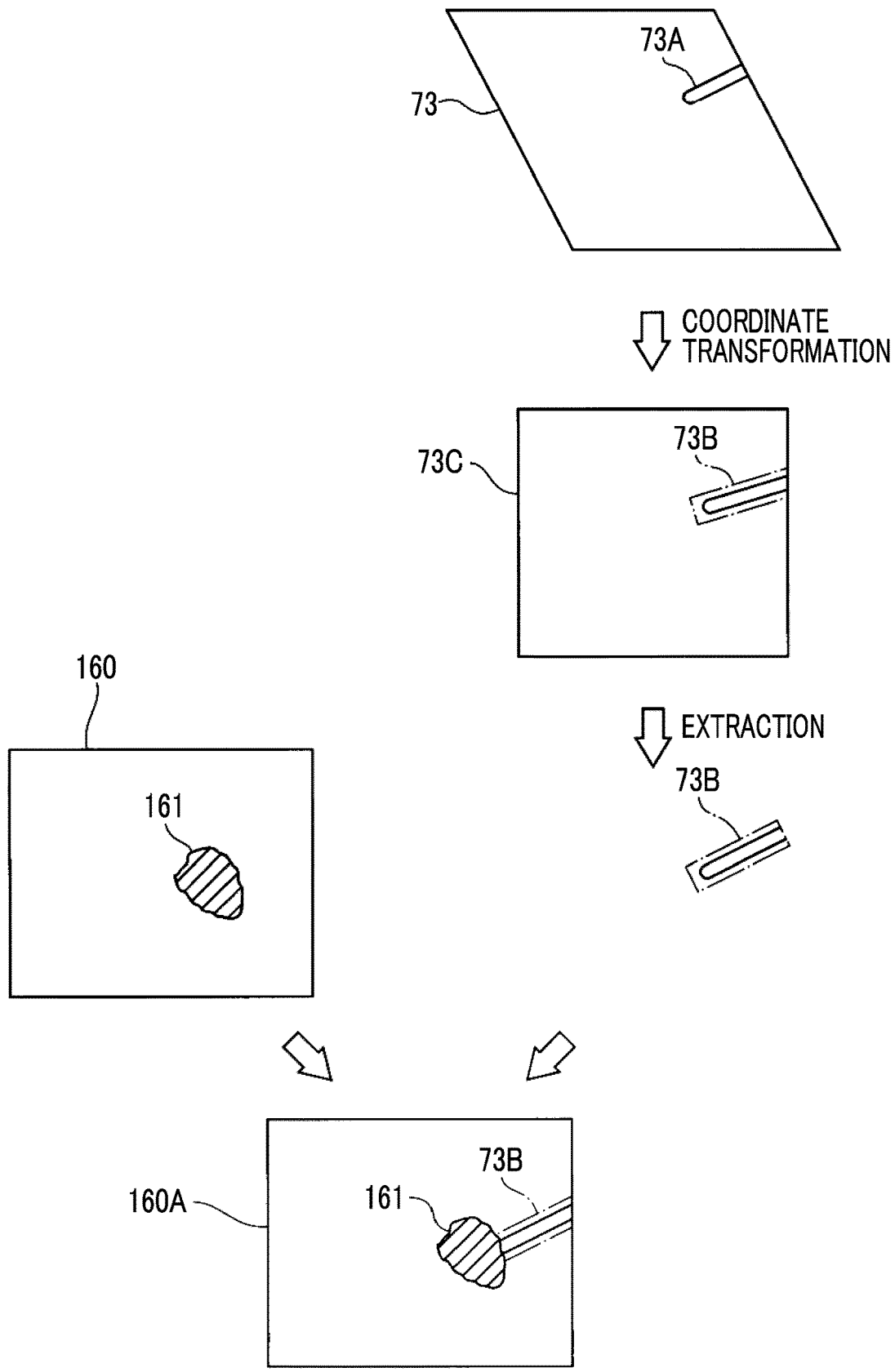
FIG. 23 shows how a second ultrasound image and a needle image are combined.

FIG. 22 is a flowchart showing the procedure of processing for combining a second ultrasound image and a needle image (processing of step 145 in FIG. 21). FIG. 23 shows how to combine a second ultrasound image and a needle image.

For example, it is assumed that the first ultrasound image 73 is selected as a needle image from a plurality of first ultrasound images 71 to 73. This also applies to a case where another first ultrasound image 71 or 72 is selected and a case where a new needle image is generated by combination. The first ultrasound image 73 determined as a needle image is coordinate-transformed by the control device 2 (step 151), and a coordinate-transformed first ultrasound image 73C is obtained. From the coordinate-transformed first ultrasound image 73C, extraction of feature points of the needle and generation of a needle candidate line are performed by the control device 2, and a region including the generated needle candidate line is detected by the control device 2 (a second needle region detection device) as the region 73B where the needle is present (step 152). Then, the region 73B where the needle is present is extracted from the coordinate-transformed first ultrasound image 73C (step 153).

In addition, as shown in FIG. 23, it is assumed that a second ultrasound image 160 is obtained. In the second ultrasound image 160, an image 161 of the tissue regarded as a lesion appears.

The second ultrasound image 160 is sequentially scanned, and in a portion other than a region corresponding to the region 73B where the needle is present (NO in step 154), a display control device 16 is controlled by the control device 2 so that the second ultrasound image 160 is displayed on a display device 17. As a result, the second ultrasound image 160 is displayed in a portion other than the region 73B where the needle is present. In a portion corresponding to the region 73B where the needle is present (YES in step 154), the display control device 16 is controlled by the control device 2 so that the image of the region 73B where the needle is present is displayed on the display device 17.

In this manner, an image 160A in which the image 161 of the tissue of the subject and the image of the region 73B where the needle is present are combined is displayed on the display device 17. The doctor inserts a needle into the tissue while observing the combined image 160A, and samples the tissue with the needle.

The image data output from the image generating device 14 is also supplied to an image memory 15, and the image data indicating the combined image 160A is stored in the image memory 15. By supplying the image data stored in the image memory 15 to the display control device 16, the combined image 160A is displayed on the display screen of the display device 17.

Figure 24:
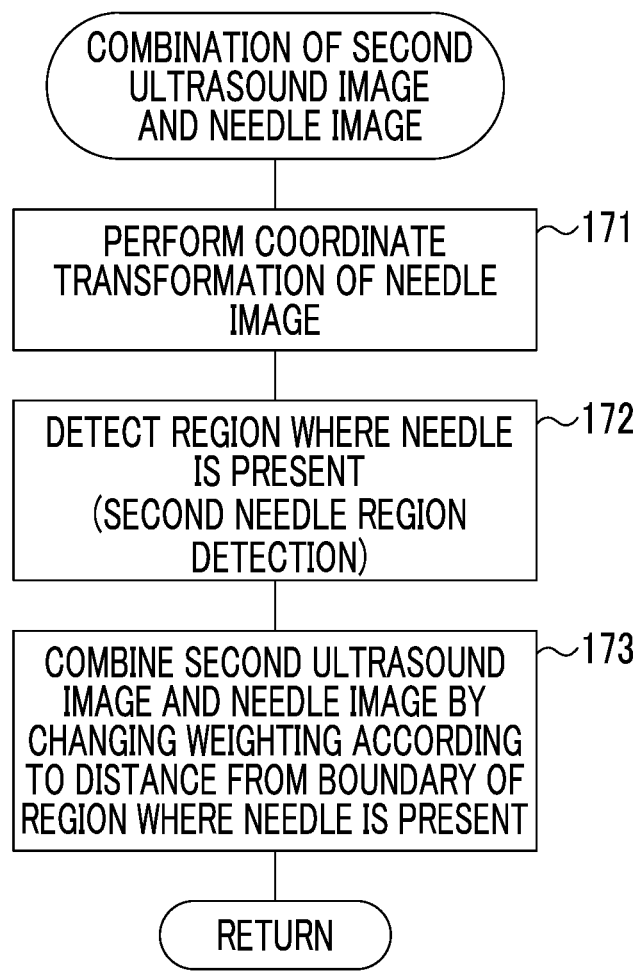
FIG. 24 is a flowchart showing the procedure of processing for combining a second ultrasound image and a needle image.

FIG. 24 is a flowchart showing another example of the processing for combining a second ultrasound image and a needle image (processing of step 145 in FIG. 21).

Although a case where the first ultrasound image 73 is selected as a needle image from a plurality of first ultrasound images 71 to 73 is taken as an example, the same applies to a case where another first ultrasound image 71 or 72 is selected or a case where a new needle image is generated by combination. The first ultrasound image 73 selected as a needle image is coordinate-transformed by the control device 2 so that the coordinates of the first ultrasound image 73 match the coordinates of the second ultrasound image 160 (step 171). The region 73B where the needle is present is detected from the coordinate-transformed first ultrasound image 73C by the control device 2 (a second needle region detection device) (step 172). The first ultrasound image 73C after the coordinate transformation and the second ultrasound image 160 are combined. In this combination, the second ultrasound image 160 and the first ultrasound image 73 selected as a needle image are combined by the image generating device 14, for example, by weighting that the image level of the first ultrasound image 73 selected as a needle image decreases and the image level of the second ultrasound image 160 increases as the distance from the boundary of the region 73B where the needle is present to the outside increases (step 173). In this manner, the weighting is changed according to the distance from the boundary of the region 73B where the needle is present, so that the second ultrasound image 160 and the first ultrasound image 73 selected as a needle image are combined.

Figure 25:
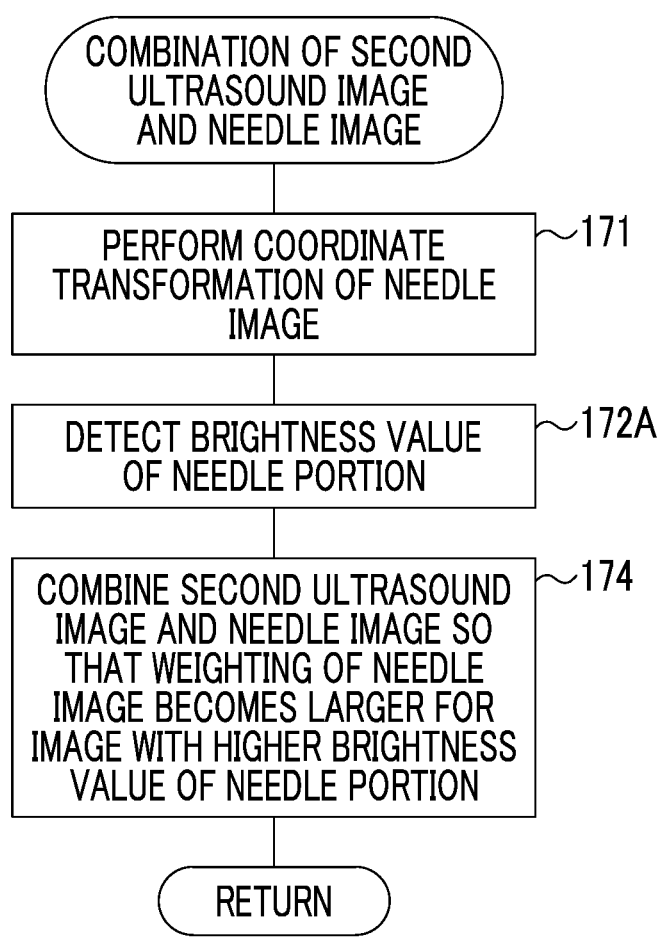
FIG. 25 is a flowchart showing the procedure of processing for combining a second ultrasound image and a needle image.

FIG. 25 is a flowchart showing still another example of the processing for combining a second ultrasound image and a needle image (processing of step 145 in FIG. 21).

It is assumed that the first ultrasound image 73 is selected as a needle image from a plurality of first ultrasound images 71 to 73. This also applies to a case where another first ultrasound image 71 or 72 is selected and a case where a new needle image is generated by combination. The first ultrasound image 73 selected as a needle image is coordinate-transformed (step 171). Then, the brightness value of a needle portion is detected from the coordinate-transformed first ultrasound image 73C (step 172A). In combination of the second ultrasound image 160 and the coordinate-transformed first ultrasound image 73C, the weighting of the first ultrasound image 73 selected as a needle image becomes larger for an image with a higher brightness value of a needle portion (step 174).

The control device 2 (a first combining device) can combine the needle image (for example, the first ultrasound image 73) and the second ultrasound image 160 with a predetermined weighting.

In addition, ultrasound waves may be transmitted in a state in which the number of ultrasound transducers that transmit the ultrasound waves 51 having an intensity distribution centered on the first direction, which is performed in the case of generating the plurality of first ultrasound images 71 to 73, is larger than the number of ultrasound transducers that transmit the ultrasound waves 51 having an intensity distribution centered on the second direction, which is performed in the case of generating the second ultrasound image 160. This is because the amount of noise received by the ultrasound transducers can be reduced by reducing the number of ultrasound transducers transmitting ultrasound waves in the case of generating the second ultrasound image 160 and accordingly a high-quality second ultrasound image can be obtained.

Figure 26:
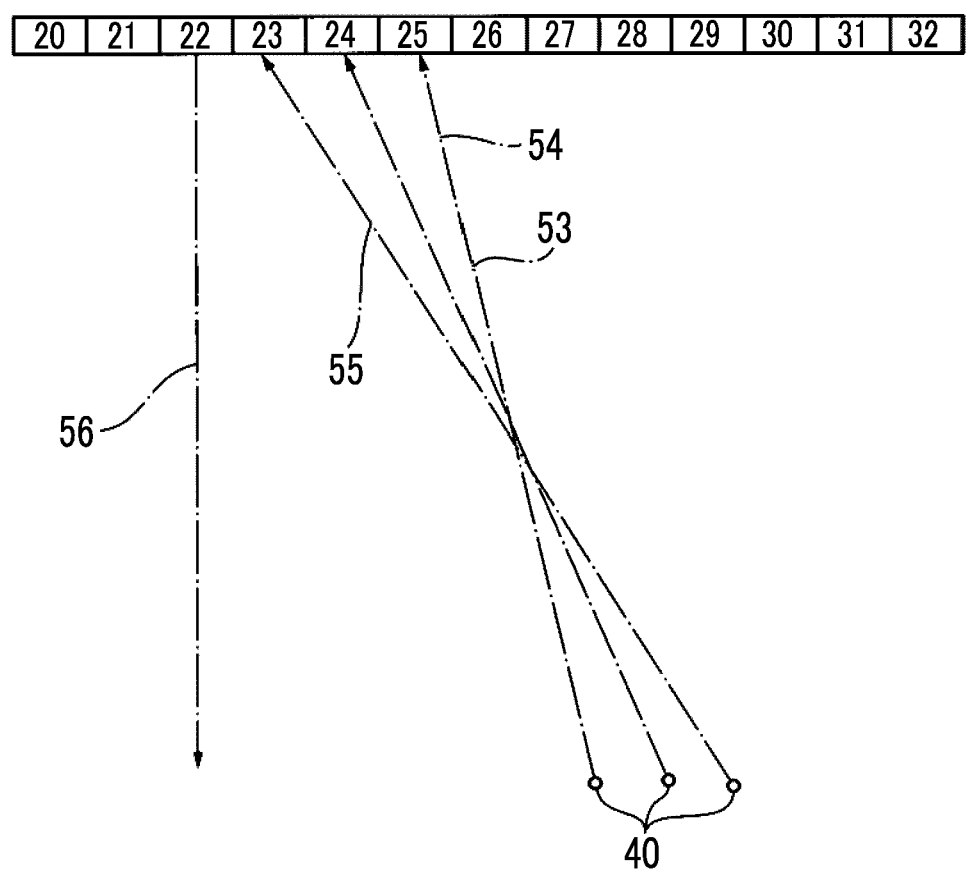
FIG. 26 shows a virtual reception direction.

FIG. 26 shows lines in the virtual reception direction.

The lines 55, 53, and 54 in the virtual reception direction serve as a reference for performing the phasing addition of ultrasound echo data, and are set by the operation device 3. However, lines in the first direction can be included within the range of the lines 55, 53, and 54 in the plurality of virtual reception directions. One of the lines 55, 53, and 54 in the plurality of virtual reception directions may match the line in the first direction.

In a case where the ultrasound probe 6 is of a linear type, it is preferable that the line in the second direction used to generate the second ultrasound image 160 is a line 56 in a direction perpendicular to each of the plurality of ultrasound transducers (in FIGS. 2A, 3, 4, 7A, and 10A, the ultrasound probe 6 has an arrangement of linear type ultrasound transducers 20 to 32). In a case where the ultrasound probe 6 is of a convex type, it is preferable that the line in the second direction is a line in a straight direction from each ultrasound transducer forming the ultrasound probe 6 (in a case where a plurality of ultrasound transducers forming the convex type ultrasound probe 6 are arranged on a circle, a direction from the center of the circle to the extension of the straight line extending to each ultrasound transducer).

It is preferable that the first direction is a direction inclined from a direction perpendicular to each of the plurality of ultrasound transducers. Therefore, in a case where the first direction is inclined with respect to the second direction and the second direction is vertical, a direction that is not parallel to the second direction is an inclined direction.

Figure 27:
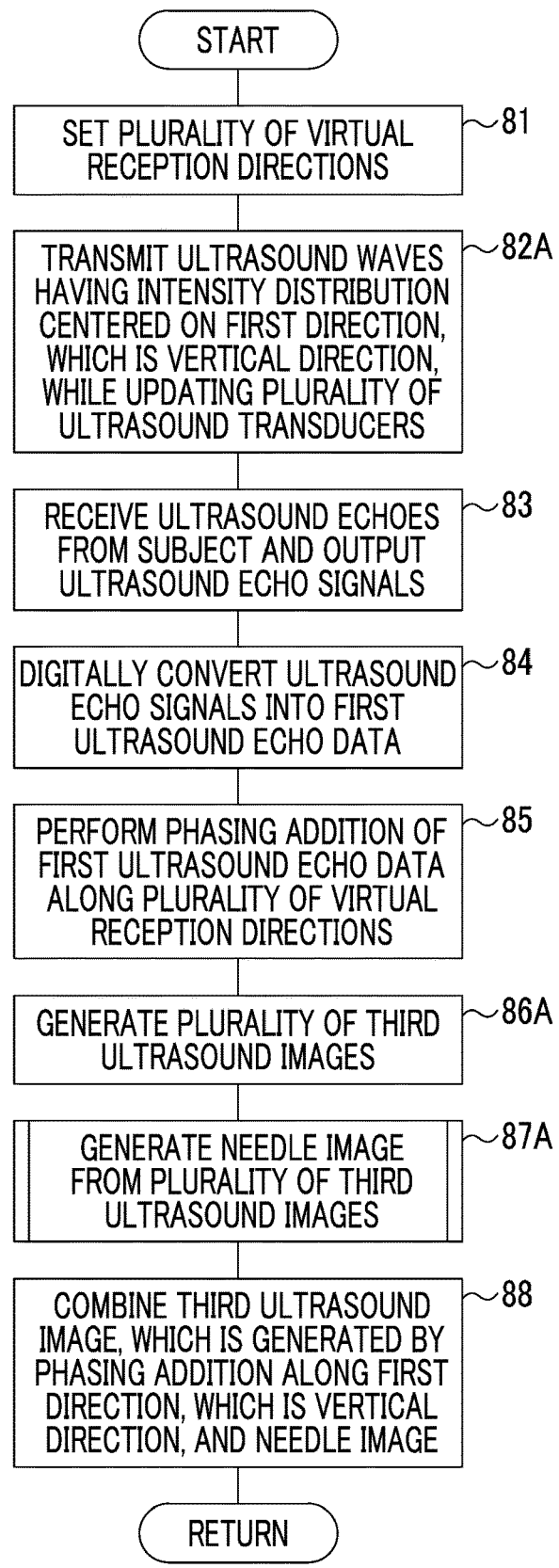
FIG. 27 is a flowchart showing the procedure of the processing of the ultrasound diagnostic apparatus.
Figure 28:
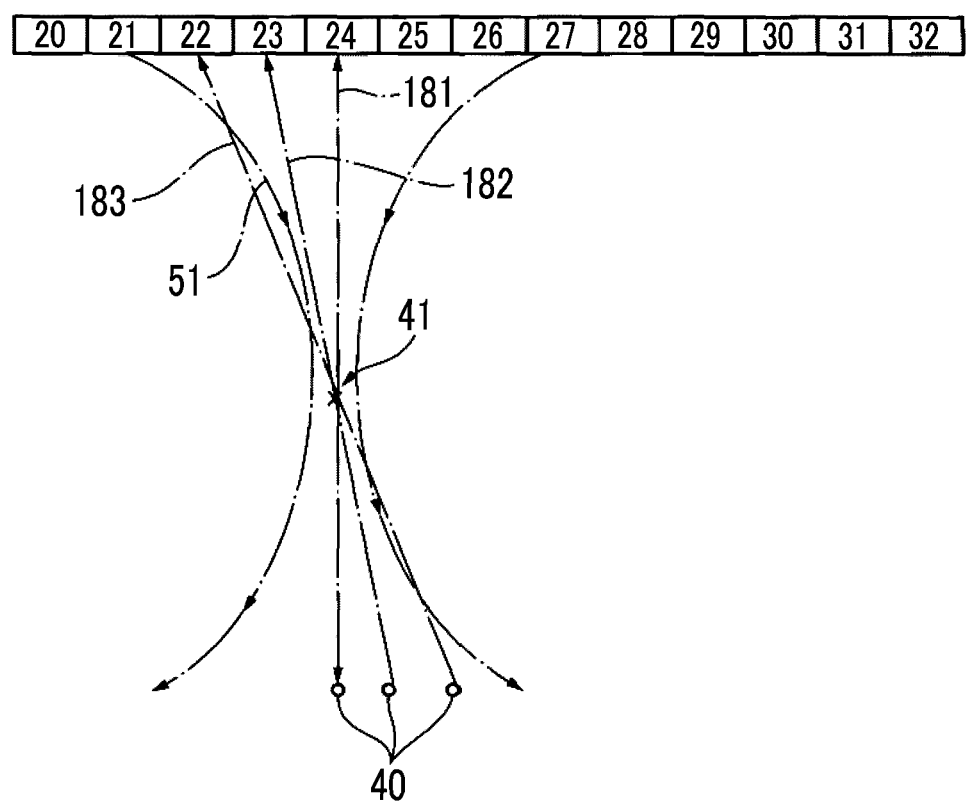
FIG. 28 shows how ultrasound waves are transmitted.
Figure 29A:
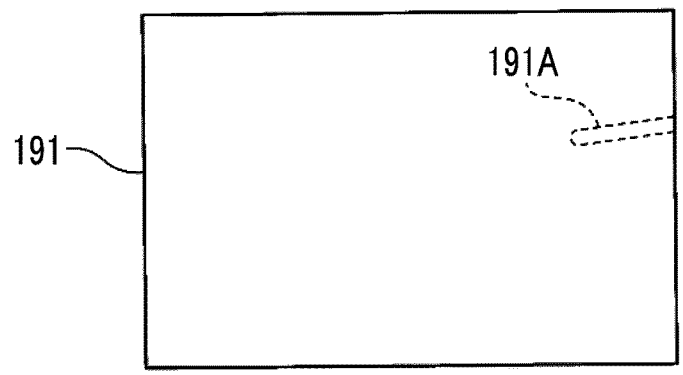
FIG. 29A shows an example of a first ultrasound image.
Figure 29B:
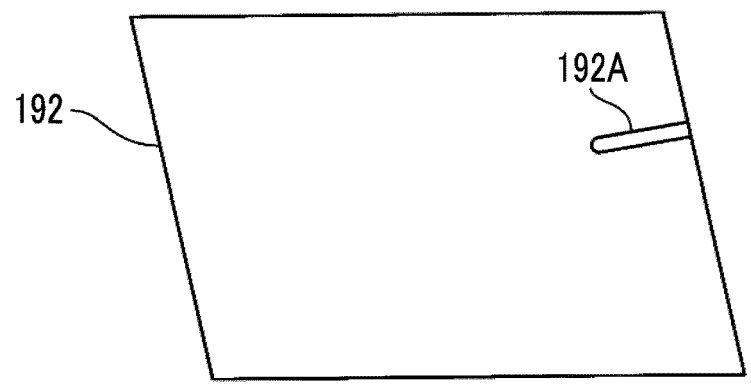
FIG. 29B shows an example of the first ultrasound image.
Figure 29C:
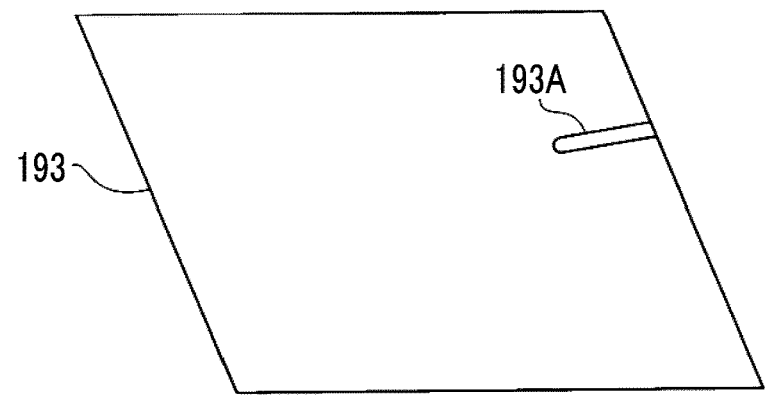
FIG. 29C shows an example of the first ultrasound image.

FIG. 27 is a flowchart showing an example of the procedure of another processing of the ultrasound diagnostic apparatus 1. In the present embodiment, the line in the first direction is the line 56 in the vertical direction (refer to FIG. 26). FIG. 28 shows how the ultrasound waves 51 are transmitted from the ultrasound transducers 21 to 27. FIGS. 29A to 29C are examples of a plurality of third ultrasound images that are generated.

A plurality of virtual reception directions are set by the operation device 3 (step 81). In the present embodiment, as shown in FIG. 28, it is assumed that virtual reception directions determined by lines 181, 182, and 183 are set by the operation device 3 (a virtual reception direction setting device). The line 181 in the virtual reception direction matches a line in the first direction that is a direction perpendicular to each of the plurality of ultrasound transducers 21 to 27. The ultrasound waves 51 having an intensity distribution centered on the first direction, which is a direction perpendicular to each of the plurality of ultrasound transducers, are transmitted from the ultrasound transducers 21 to 27 while updating the plurality of ultrasound transducers (step 82A). The ultrasound waves 51 converge on the focusing position 41, ultrasound echoes from the observation target position 40 of the subject are received by the ultrasound transducers 21 to 27, and ultrasound echo signals are output from the ultrasound transducers 21 to 27 and the like (step 83).

The plurality of ultrasound echo signals output from the ultrasound transducers 21 to 27 are digitally converted into first ultrasound echo data by the A/D conversion circuit 8 (step 84). In the phasing addition device 11, phasing addition is performed along the lines 181, 182, and 183 in the plurality of virtual reception directions (step 85). As shown in FIGS. 29A, 29B, and 29C, a plurality of third ultrasound images 191, 192, and 193 are generated (step 86A).

Portions 191A, 192A, and 193A of the needle are included in the plurality of generated third ultrasound images 191, 192, and 193, respectively. A needle image is generated using the third ultrasound images 191, 192, and 193 (step 87A). The third ultrasound image 191 (refer to FIG. 29A; an ultrasound image suitable for displaying the tissue, such as the second ultrasound image 160) generated by phasing addition along the line in the first direction that is a vertical direction and the needle image are combined by the image generating device 14 (a second combining device) (step 88).

In this manner, the third ultrasound image 191 suitable for displaying the tissue and the needle image, in which it is easy to see the needle, can be generated by driving the ultrasound probe 6 once.

FIGS. 30 to 41C show another embodiment, in which the ultrasound probe 6 is of a convex type.

FIGS. 30 to 35C show cases where the first direction is straight from each of the ultrasound transducers 20 to 32 (assuming that the ultrasound transducers 20 to 32 arranged in an arc shape are arranged on the circumference, a direction extending from the center of the circle to each of the ultrasound transducers 20 to 32 matches the first direction).

Figure 30:
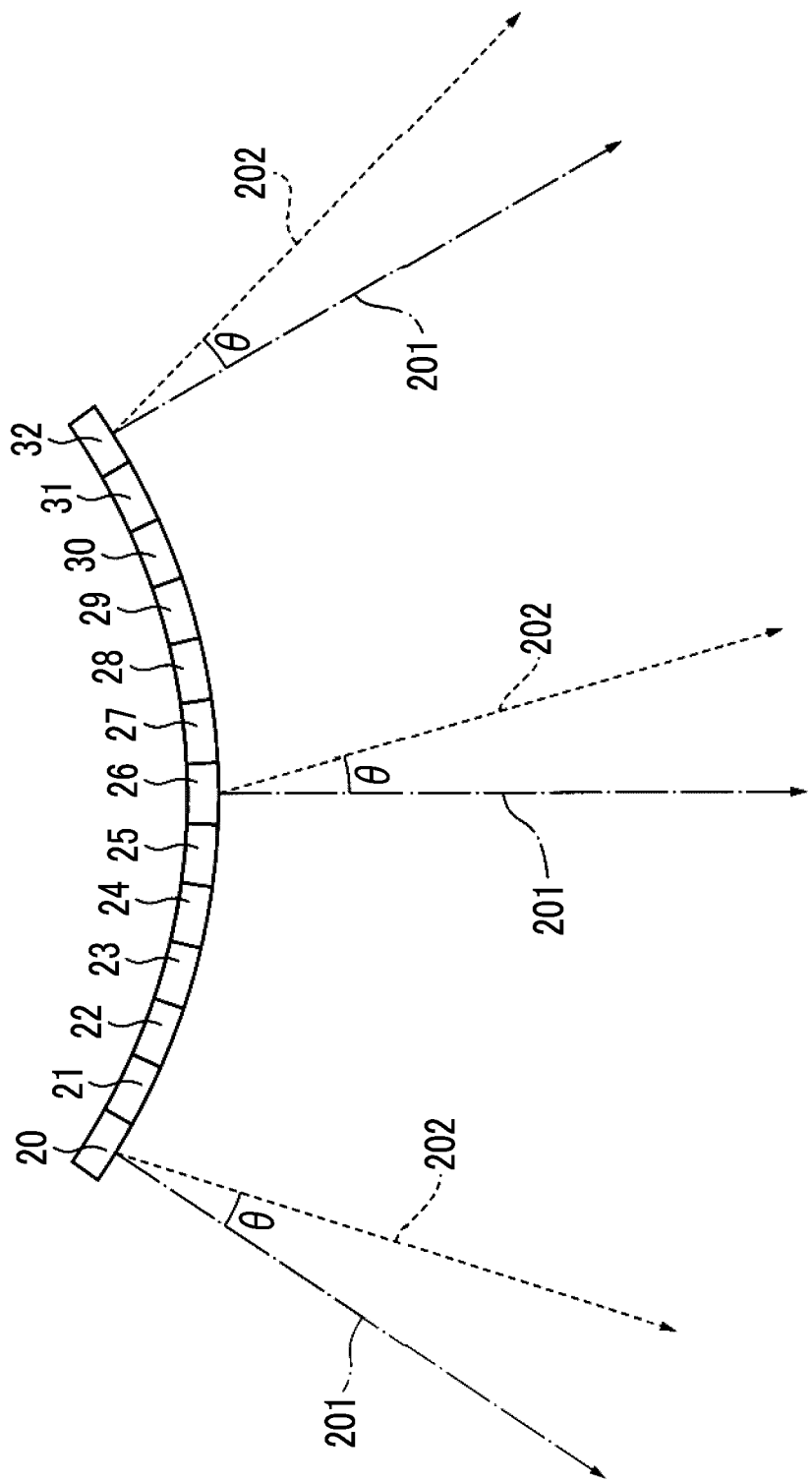
FIG. 30 shows directions in which ultrasound waves are transmitted from ultrasound transducers.

FIG. 30 shows the relationship between each of the ultrasound transducers 20 to 32 and a line 201 in the first direction.

The line 201 in the first direction is a direction extending straight from each of the ultrasound transducers 20 to 32. A line 202 in the virtual reception direction is inclined by an angle θ from the line 201 in the first direction.

Figure 31A:
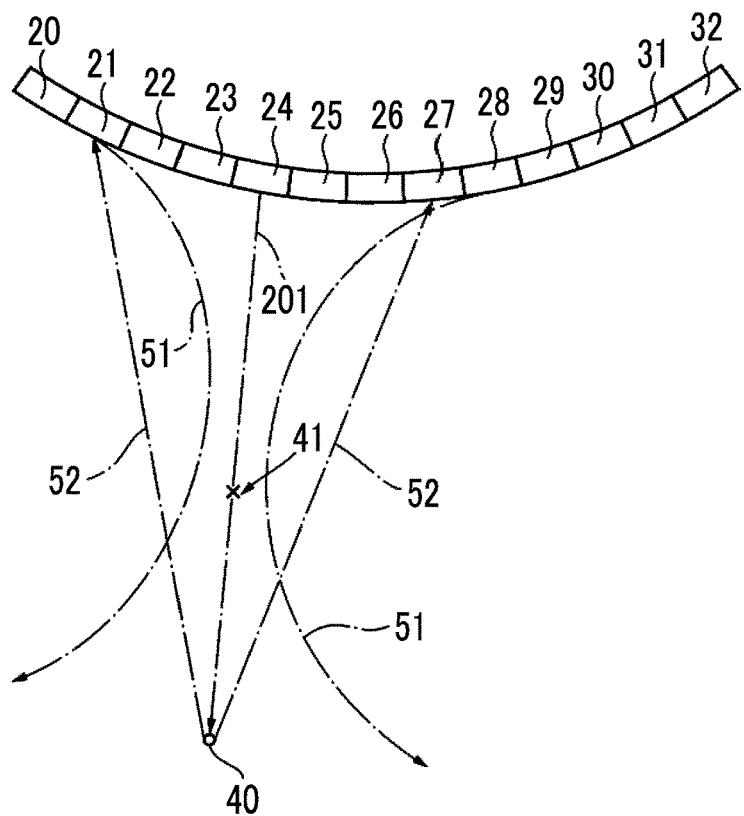
FIG. 31A shows how ultrasound waves are transmitted from ultrasound transducers.

FIG. 31A corresponds to FIG. 2A, and shows how the ultrasound waves 51 converging on the focusing position 41 are transmitted from the ultrasound transducers 21 to 27.

The ultrasound waves 51 have an intensity distribution centered on the first direction determined by the line 201. By the transmission of the ultrasound waves 51, the ultrasound echoes 52 are generated from the observation target position 40. The generated ultrasound echoes 52 are received by the ultrasound transducers 21 to 27. Ultrasound echo signals 211 to 217 (refer to FIG. 31B) are output from the ultrasound transducers 21 to 27.

Figure 31B:
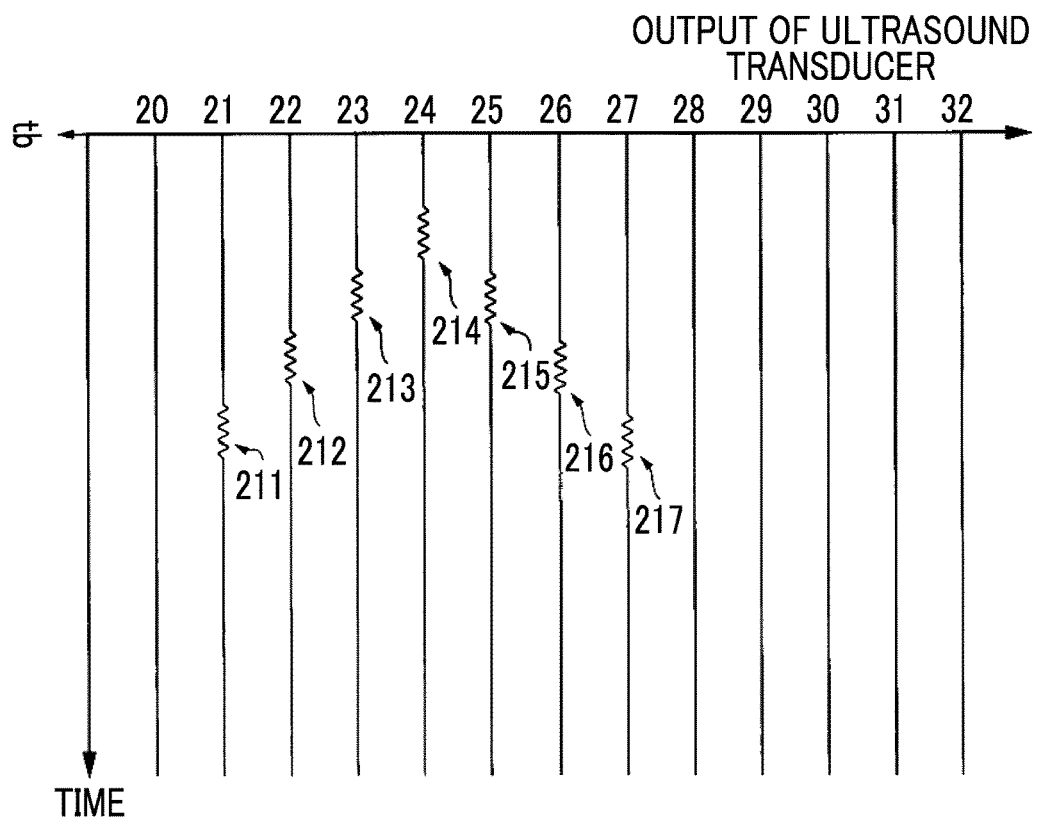
FIG. 31B shows ultrasound echo signals.

FIG. 31B corresponds to FIG. 2B, and shows the ultrasound echo signals 211 to 217 output from the ultrasound transducers 21 to 27.

Depending on the positions of the ultrasound transducers 21 to 27, the output timings of the ultrasound echo signals 211 to 217 are different. First, the ultrasound echo signal 214 from the ultrasound transducer 24 is output. Then, the ultrasound echo signals 213 and 215 from the ultrasound transducers 23 and 25 are output. Then, the ultrasound echo signals 212 and 216 from the ultrasound transducers 22 and 26 are output. Finally, the ultrasound echo signals 211 and 217 from the ultrasound transducers 21 and 27 are output.

The ultrasound echo signals 211 to 217 obtained as described above are digitally converted into ultrasound echo data by the A/D conversion circuit 8 and are phased and added along the line 201 in the first direction (after the output time difference of the ultrasound echo signals 211 to 217 is corrected, first ultrasound echo data obtained by digitally converting the ultrasound echo signals 211 to 217 is superimposed on ultrasound echo data obtained by digitally converting the ultrasound echo signal 214).

Figure 32A:
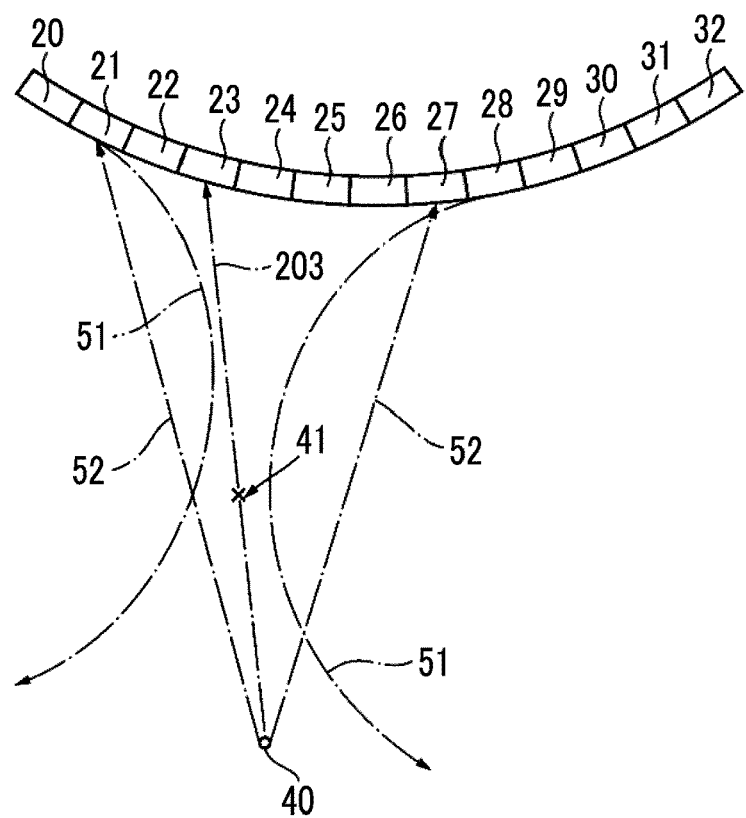
FIG. 32A shows how ultrasound waves are transmitted from ultrasound transducers.
Figure 32B:
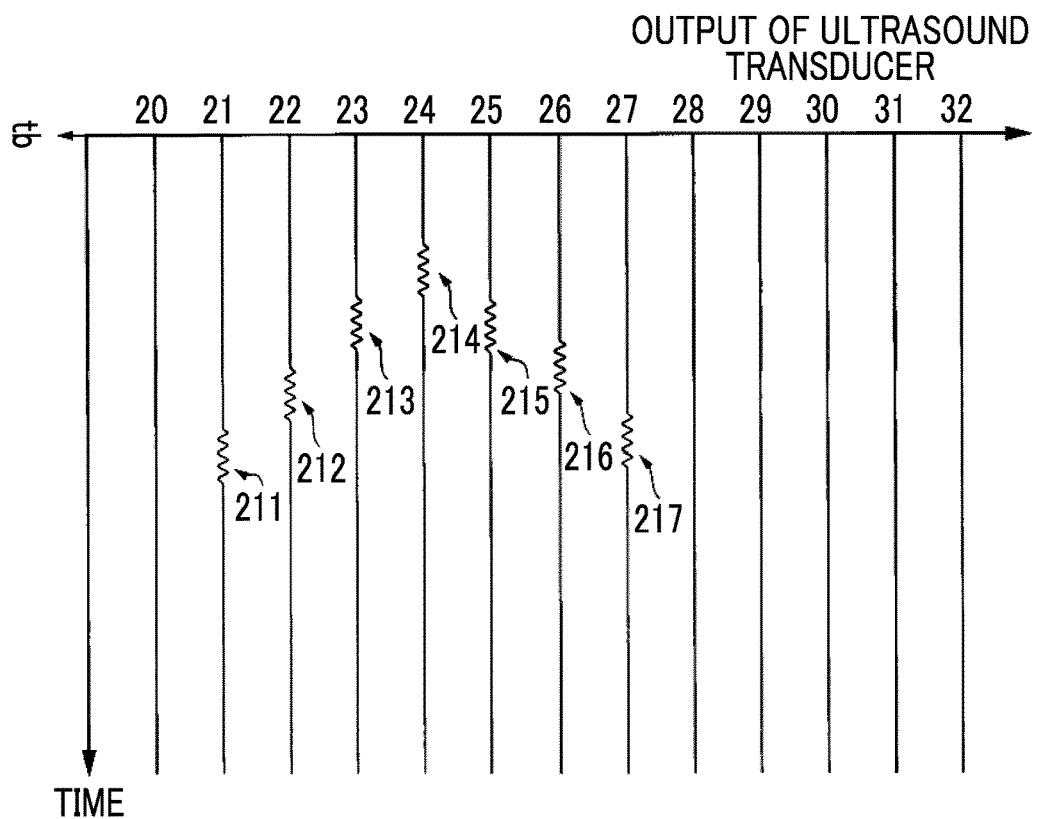
FIG. 32B shows ultrasound echo signals.

FIG. 32A corresponds to FIG. 10A, and shows how the ultrasound waves 51 converging on the focusing position 41 are transmitted from the ultrasound transducers 21 to 27. FIG. 32B shows the ultrasound echo signals 211 to 217 output from the ultrasound transducers 21 to 27.

As shown in FIG. 32A, a line 203 in the virtual reception direction is set.

The ultrasound echo signals 211 to 217 are output from the ultrasound transducers 21 to 27 at the output timings corresponding to the positions of the ultrasound transducers 21 to 27. The ultrasound echo signals 211 to 217 obtained as described above are digitally converted into ultrasound echo data by the A/D conversion circuit 8 and are phased and added along the line 203 in the virtual reception direction (after the output time difference of the ultrasound echo signals 211 to 217 is corrected, first ultrasound echo data obtained by digitally converting the ultrasound echo signals 211 to 217 is superimposed on ultrasound echo data obtained by digitally converting the ultrasound echo signal 213).

Figure 33A:
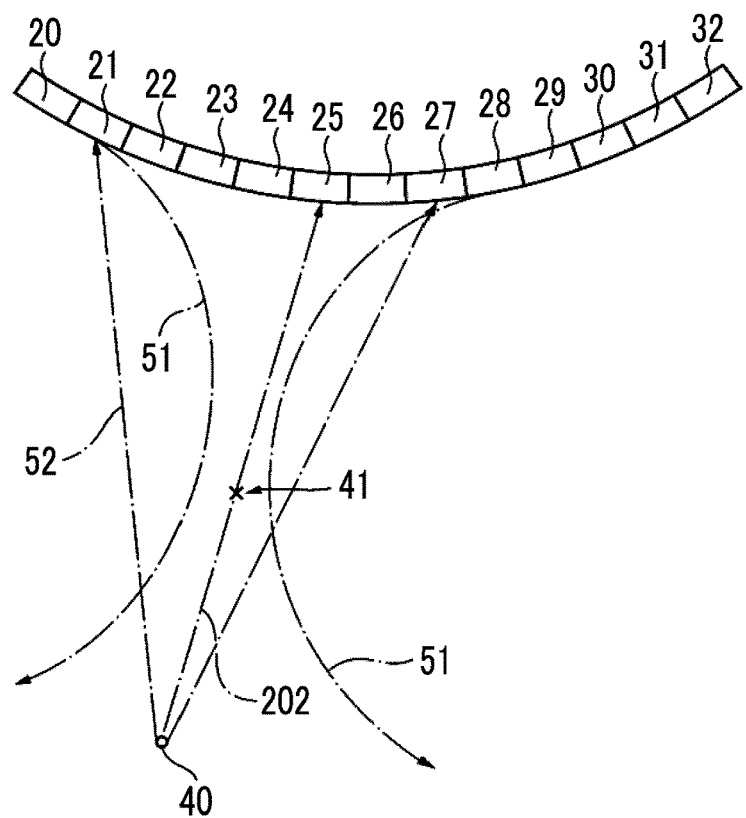
FIG. 33A shows how ultrasound waves are transmitted from ultrasound transducers.
Figure 33B:
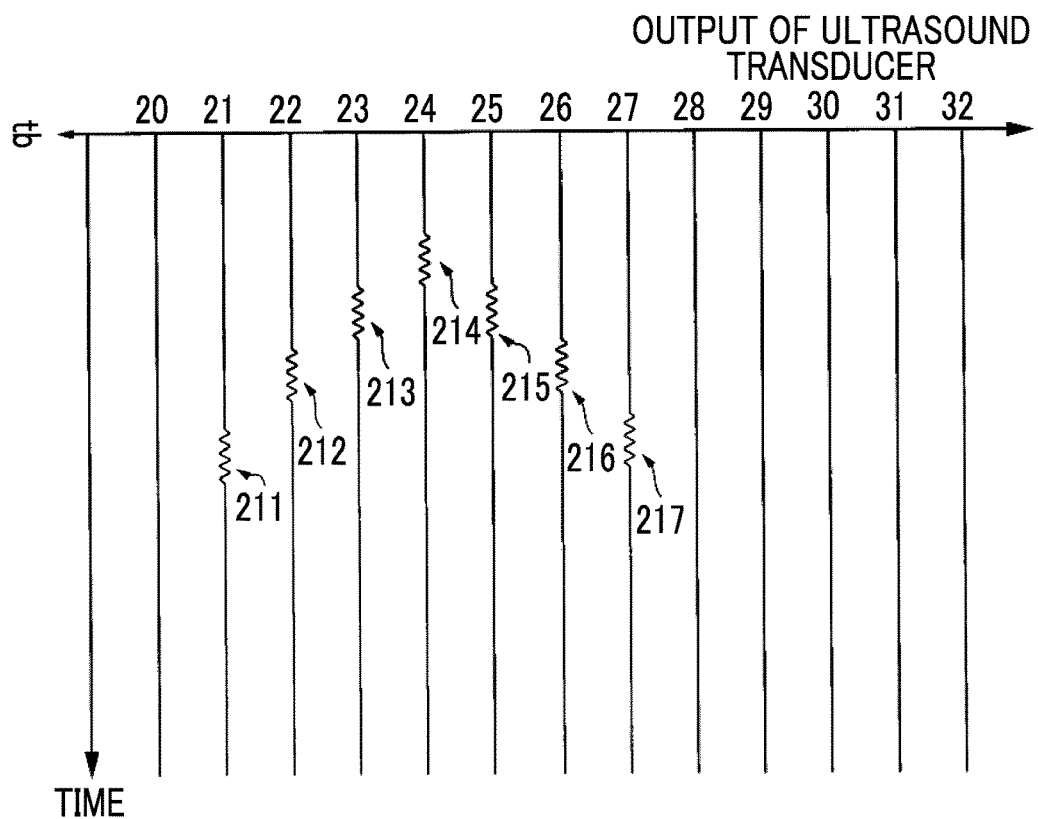
FIG. 33B shows ultrasound echo signals.

FIG. 33A corresponds to FIG. 7A, and shows how the ultrasound waves 51 converging on the focusing position 41 are transmitted from the ultrasound transducers 21 to 27. FIG. 33B shows the ultrasound echo signals 211 to 217 output from the ultrasound transducers 21 to 27.

As shown in FIG. 33A, the line 202 in the virtual reception direction is set.

The ultrasound echo signals 211 to 217 are output from the ultrasound transducers 21 to 27 at the output timings corresponding to the positions of the ultrasound transducers 21 to 27. The ultrasound echo signals 211 to 217 obtained as described above are digitally converted into ultrasound echo data by the A/D conversion circuit 8 and are phased and added along the line 202 in the virtual reception direction (after the output time difference of the ultrasound echo signals 211 to 217 is corrected, first ultrasound echo data obtained by digitally converting the ultrasound echo signals 211 to 217 is superimposed on ultrasound echo data obtained by digitally converting the ultrasound echo signal 215).

Figure 34:
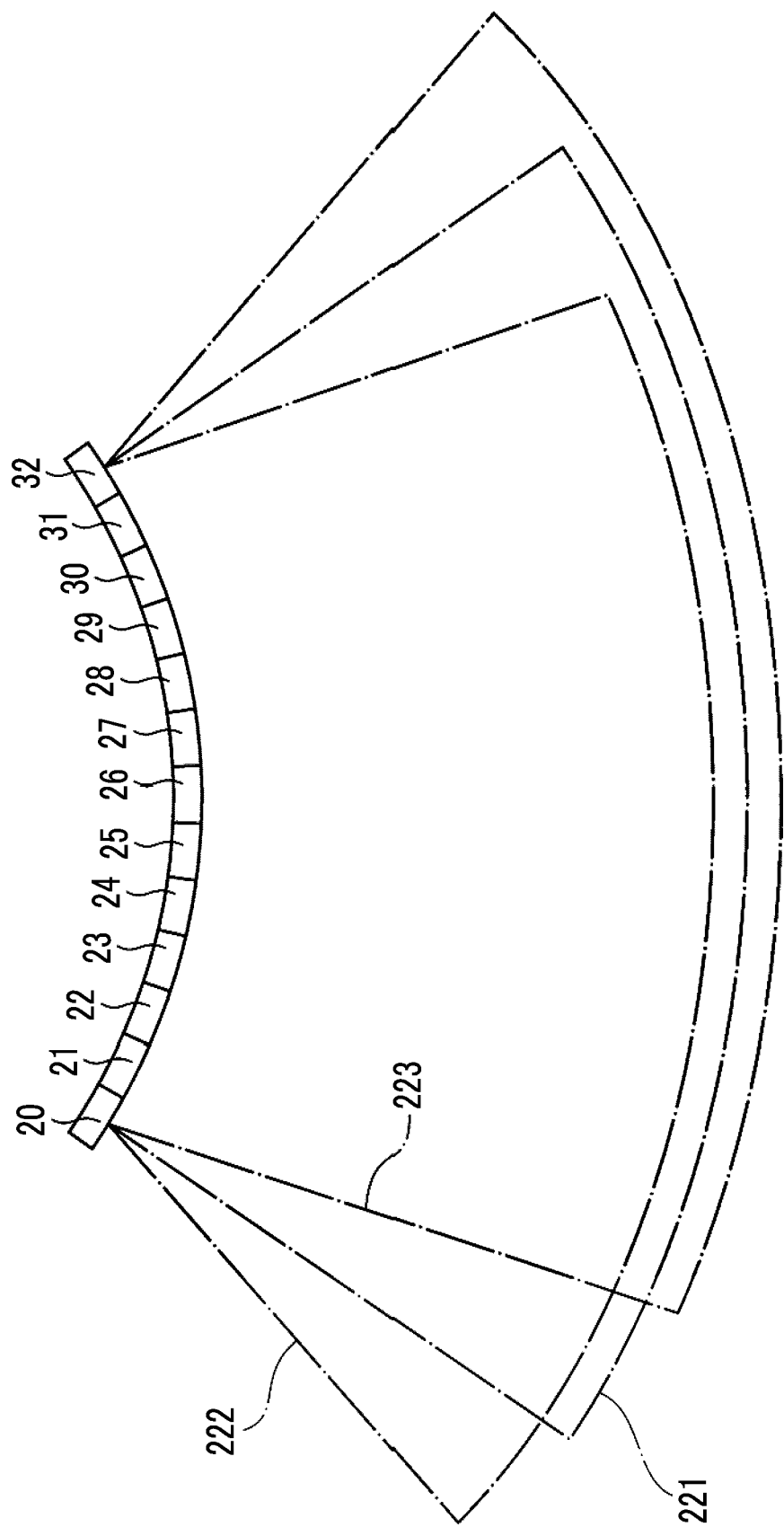
FIG. 34 shows how a plurality of first ultrasound images are generated.

FIG. 34 shows a state in which a plurality of ultrasound transducers transmitting the ultrasound waves 51 are updated in an arc direction in which the ultrasound transducers 20 to 27 are arranged, and corresponds to FIG. 13.

In a case where a plurality of ultrasound transducers transmitting the ultrasound waves 51 are updated in the arc direction in which the ultrasound transducers 20 to 27 are arranged, a plurality of first ultrasound images 221 to 223 are obtained.

Figure 35A:
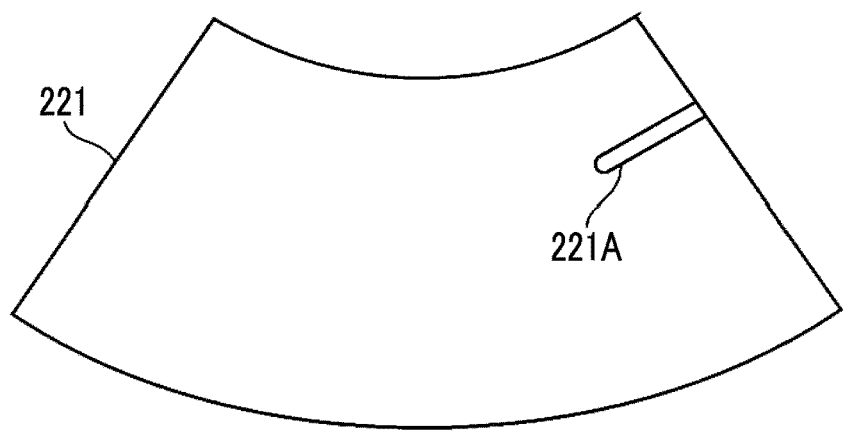
FIG. 35A shows an example of the first ultrasound image.

FIG. 35A shows the first ultrasound image 221 among the plurality of first ultrasound images 221 to 223.

In the first ultrasound image 221, the line 201 in the first direction matches a line in the virtual reception direction. A portion 221A of the needle is included in the first ultrasound image 221.

Figure 35B:
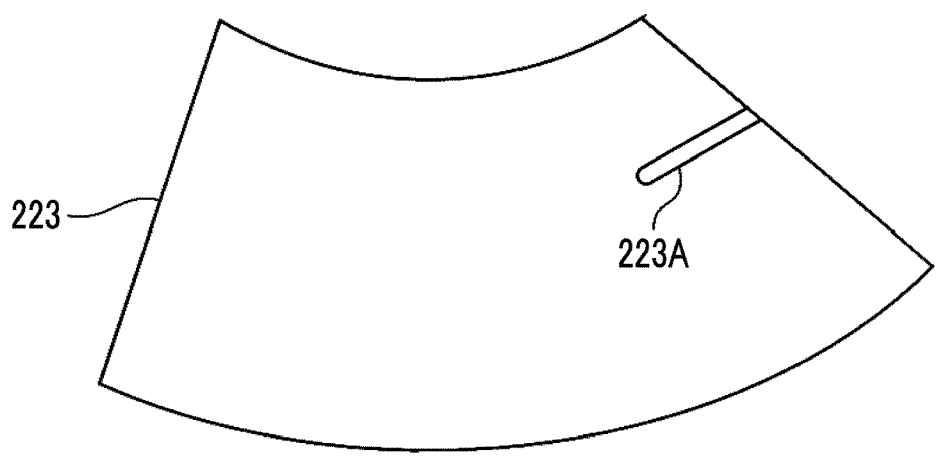
FIG. 35B shows an example of the first ultrasound image.

FIG. 35B shows the first ultrasound image 223 among the plurality of first ultrasound images 221 to 223.

The first ultrasound image 223 is obtained by performing phasing addition along the line 203 in the virtual reception direction shown in FIG. 32A. A portion 223A of the needle is included in the first ultrasound image 223.

Figure 35C:
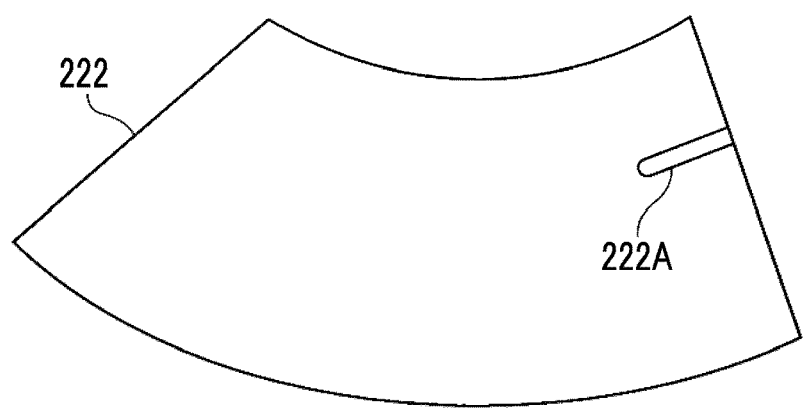
FIG. 35C shows an example of the first ultrasound image.

FIG. 35C shows the first ultrasound image 222 among the plurality of first ultrasound images 221 to 223.

The first ultrasound image 222 is obtained by performing phasing addition along the line 202 in the virtual reception direction shown in FIG. 33A. A portion 222A of the needle is included in the first ultrasound image 222.

By acquiring the plurality of first ultrasound images 221 to 223, a needle image in which it is easy to see the needle is generated (newly generated, selected, or the like). The first ultrasound image 221 is suitable for displaying the tissue since the line 201 in the virtual reception direction is a straight direction from each of the ultrasound transducers 20 to 32. Therefore, the first ultrasound image 221 can be combined with the generated needle image.

In FIGS. 36 to 41C, the first direction is parallel to a direction extending straight from the ultrasound transducer 26 at the center of the ultrasound probe 6 (assuming that the ultrasound transducers 20 to 32 are arranged on a circle, a direction extending from the center of the circle to the central ultrasound transducer 26).

Figure 36:
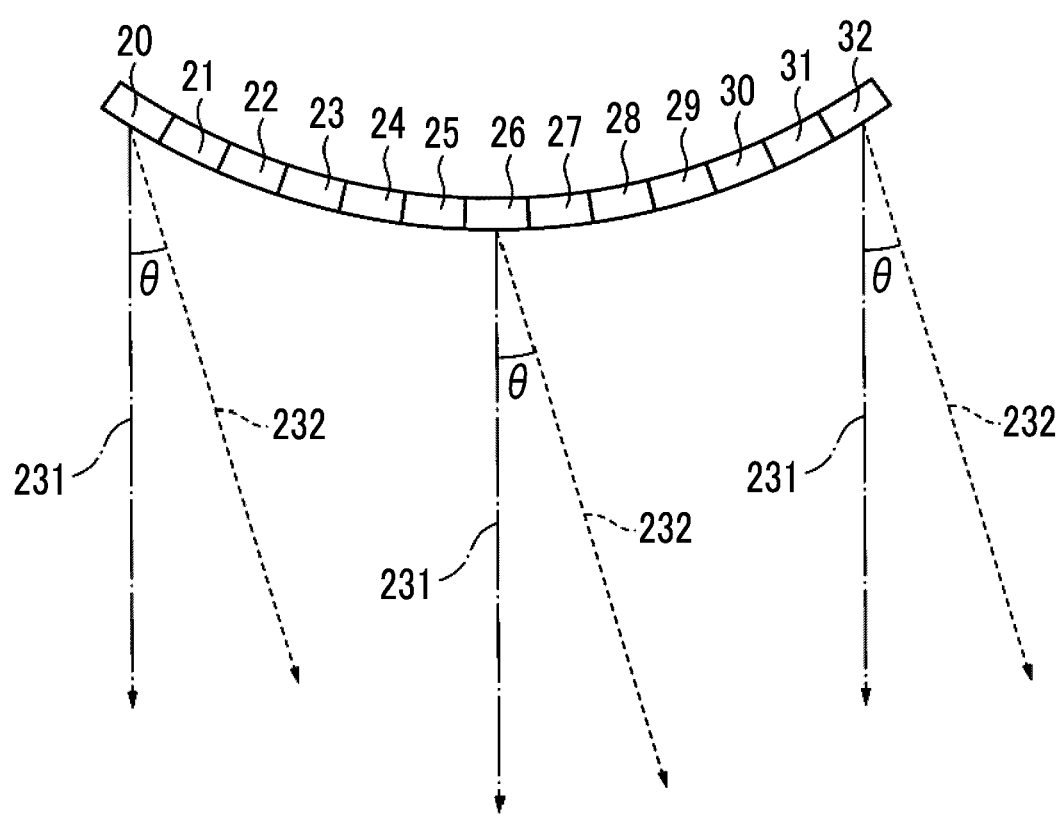
FIG. 36 shows directions in which ultrasound waves are transmitted from ultrasound transducers.

FIG. 36 shows the relationship between each of the ultrasound transducers 20 to 32 and a line 231 in the first direction.

The line 231 in the first direction is a direction extending straight from the ultrasound transducer 26 located at the center of the ultrasound transducers 20 to 32. A line 232 in the virtual reception direction is inclined by the angle θ from the line 231 in the first direction.

Figure 37A:
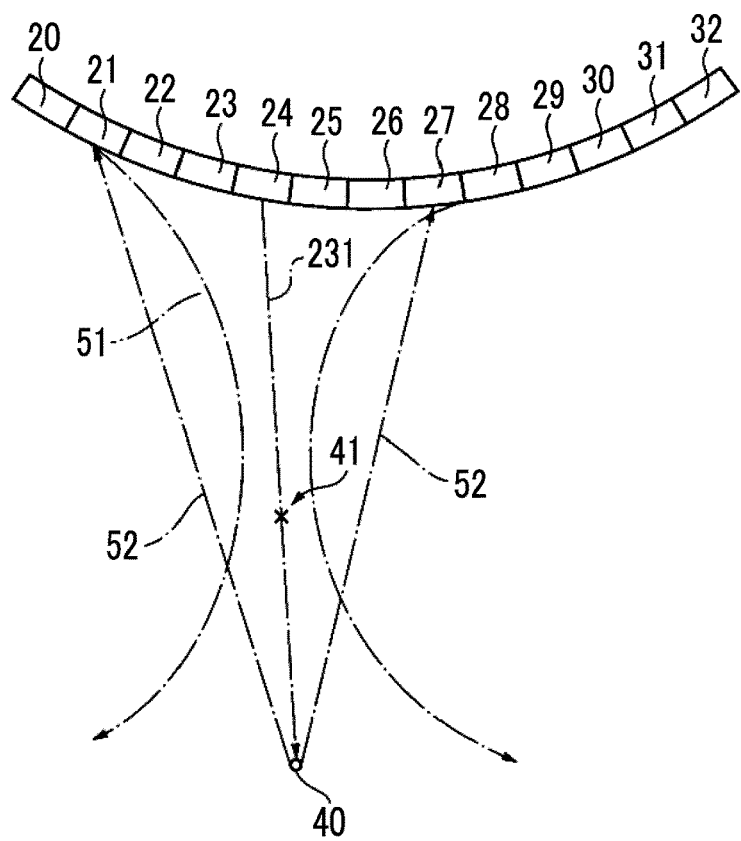
FIG. 37A shows how ultrasound waves are transmitted from ultrasound transducers.

FIG. 37A corresponds to FIG. 31A, and shows how the ultrasound waves 51 converging on the focusing position 41 are transmitted from the ultrasound transducers 21 to 27.

The ultrasound waves 51 have an intensity distribution centered on the first direction determined by the line 231. By the transmission of the ultrasound waves 51, the ultrasound echoes 52 are generated from the observation target position 40. The generated ultrasound echoes 52 are received by the ultrasound transducers 21 to 27. The ultrasound echo signals 211 to 217 (refer to FIG. 37B) are output from the ultrasound transducers 21 to 27.

Figure 37B:
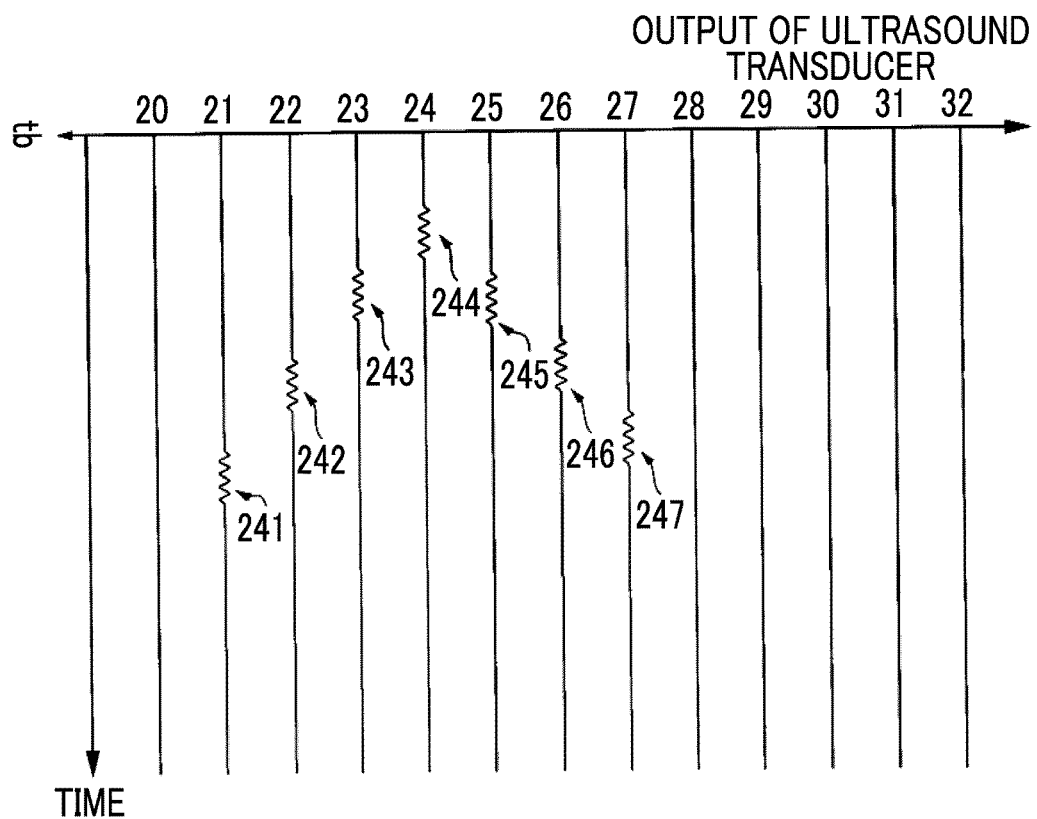
FIG. 37B shows ultrasound echo signals.

FIG. 37B corresponds to FIG. 31B, and shows ultrasound echo signals 241 to 247 output from the ultrasound transducers 21 to 27.

Depending on the positions of the ultrasound transducers 21 to 27, the output timings of the ultrasound echo signals 211 to 217 are different. First, the ultrasound echo signal 244 from the ultrasound transducer 24 is output. Then, the ultrasound echo signals 243 and 245 from the ultrasound transducers 23 and 25 are output. Then, the ultrasound echo signals 242 and 246 from the ultrasound transducers 22 and 26 are output. Finally, the ultrasound echo signals 241 and 247 from the ultrasound transducers 21 and 27 are output.

The ultrasound echo signals 241 to 247 are digitally converted into ultrasound echo data by the A/D conversion circuit 8 and are phased and added along the line 231 in the first direction (after the output time difference of the ultrasound echo signals 241 to 247 is corrected, first ultrasound echo data obtained by digitally converting the ultrasound echo signals 241 to 247 is superimposed on ultrasound echo data obtained by digitally converting the ultrasound echo signal 244).

Figure 38A:
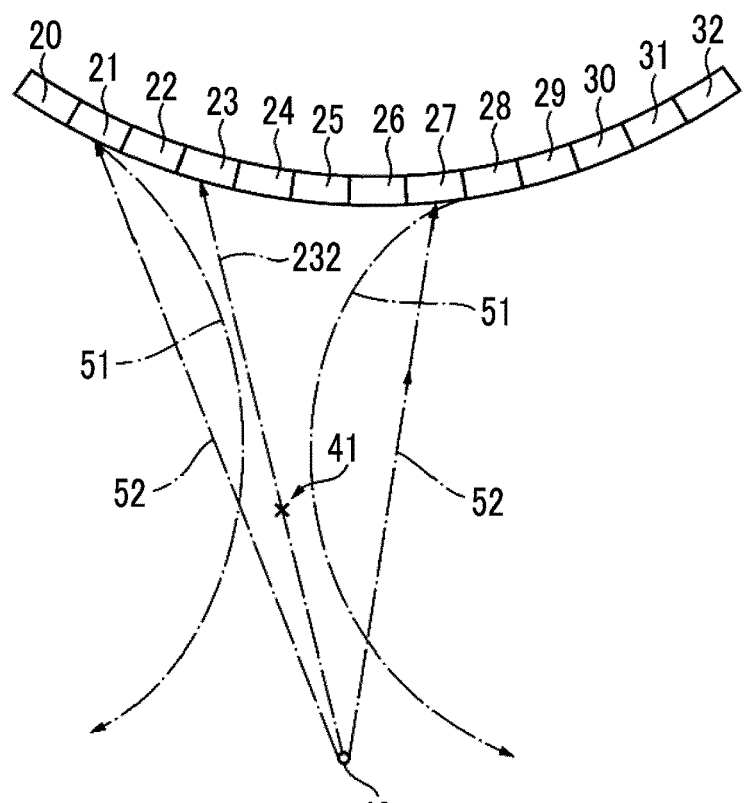
FIG. 38A shows how ultrasound waves are transmitted from ultrasound transducers.
Figure 38B:
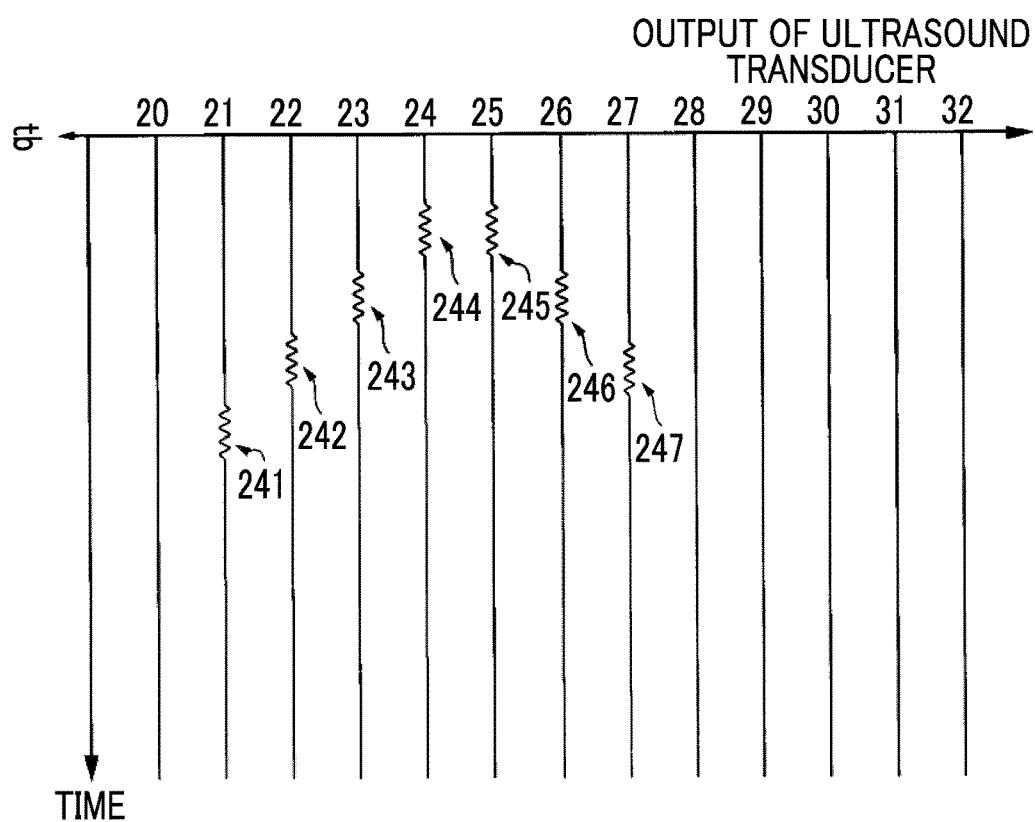
FIG. 38B shows ultrasound echo signals.

FIG. 38A corresponds to FIG. 32A, and shows how the ultrasound waves 51 converging on the focusing position 41 are transmitted from the ultrasound transducers 21 to 27. FIG. 38B shows the ultrasound echo signals 241 to 247 output from the ultrasound transducers 21 to 27.

As shown in FIG. 38A, the line 232 in the virtual reception direction is set.

The ultrasound echo signals 241 to 247 are output from the ultrasound transducers 21 to 27 at the output timings corresponding to the positions of the ultrasound transducers 21 to 27. The ultrasound echo signals 241 to 247 obtained as described above are digitally converted into ultrasound echo data by the A/D conversion circuit 8 and are phased and added along the line 232 in the virtual reception direction (after the output time difference of the ultrasound echo signals 241 to 247 is corrected, first ultrasound echo data obtained by digitally converting the ultrasound echo signals 241 to 247 is superimposed on ultrasound echo data obtained by digitally converting the ultrasound echo signal 243).

Figure 39A:
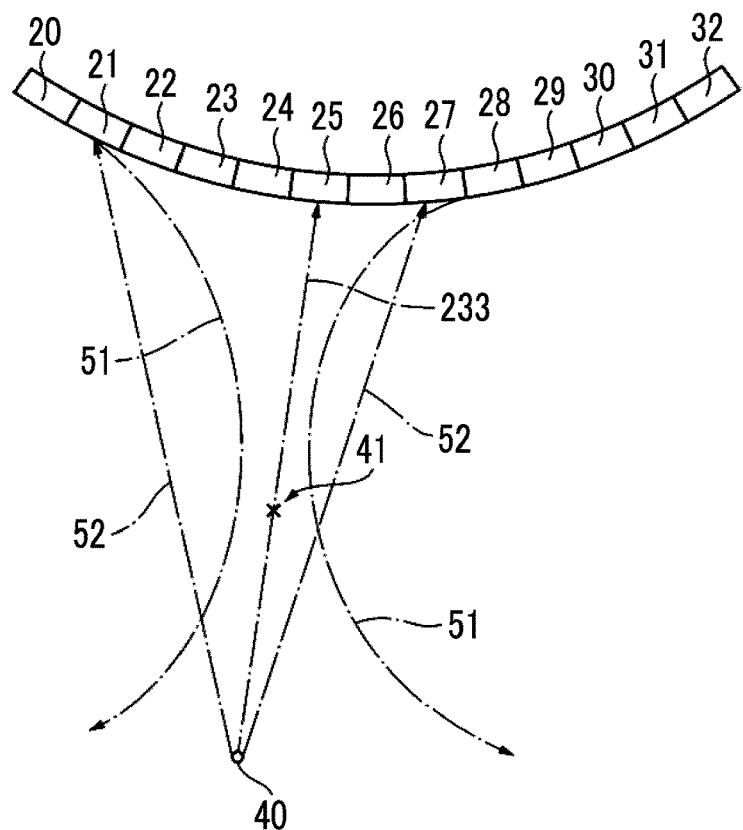
FIG. 39A shows how ultrasound waves are transmitted from ultrasound transducers.
Figure 39B:
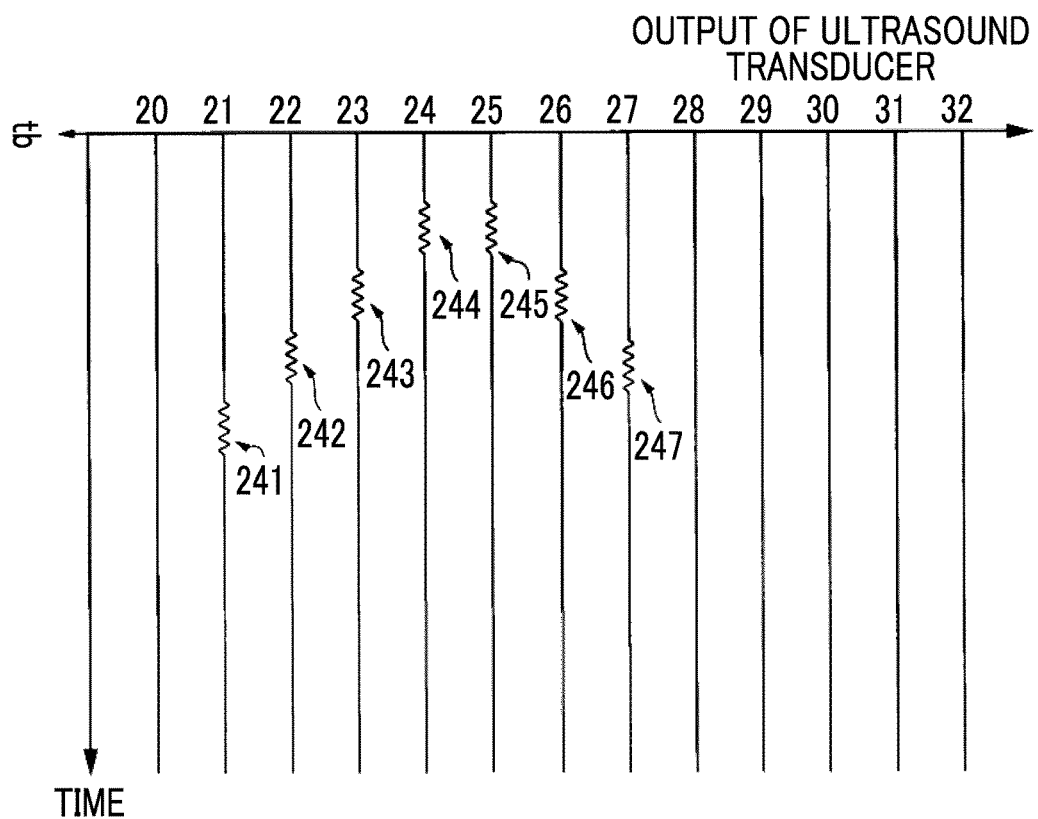
FIG. 39B shows ultrasound echo signals.

FIG. 39A corresponds to FIG. 33A, and shows how the ultrasound waves 51 converging on the focusing position 41 are transmitted from the ultrasound transducers 21 to 27. FIG. 39B shows the ultrasound echo signals 241 to 247 output from the ultrasound transducers 21 to 27.

As shown in FIG. 39A, a line 233 in the virtual reception direction is set.

The ultrasound echo signals 241 to 247 are output from the ultrasound transducers 21 to 27 at the output timings corresponding to the positions of the ultrasound transducers 21 to 27. The ultrasound echo signals 241 to 247 obtained as described above are digitally converted into ultrasound echo data by the A/D conversion circuit 8 and are phased and added along the line 233 in the virtual reception direction (after the output time difference of the ultrasound echo signals 241 to 247 is corrected, first ultrasound echo data obtained by digitally converting the ultrasound echo signals 241 to 247 is superimposed on ultrasound echo data obtained by digitally converting the ultrasound echo signal 245).

Figure 40:
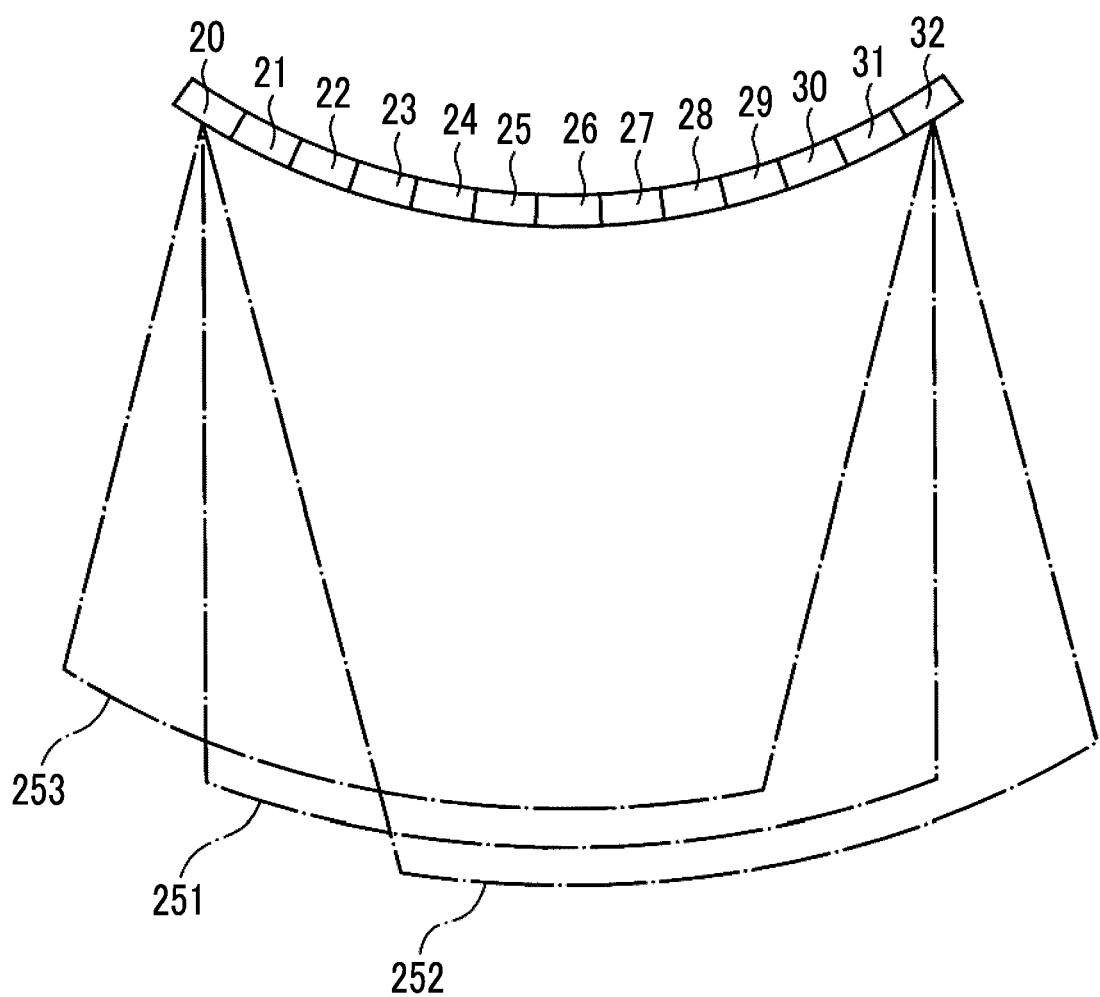
FIG. 40 shows how a plurality of first ultrasound images are generated.

FIG. 40 shows a state in which a plurality of ultrasound transducers transmitting the ultrasound waves 51 are updated in an arc direction in which the ultrasound transducers 20 to 27 are arranged, and corresponds to FIG. 34.

By updating a plurality of ultrasound transducers transmitting the ultrasound waves 51 in the arc direction in which the ultrasound transducers 20 to 27 are arranged, a plurality of first ultrasound images 251 to 253 corresponding to the plurality of first ultrasound images 71 to 73 are obtained.

Figure 41A:
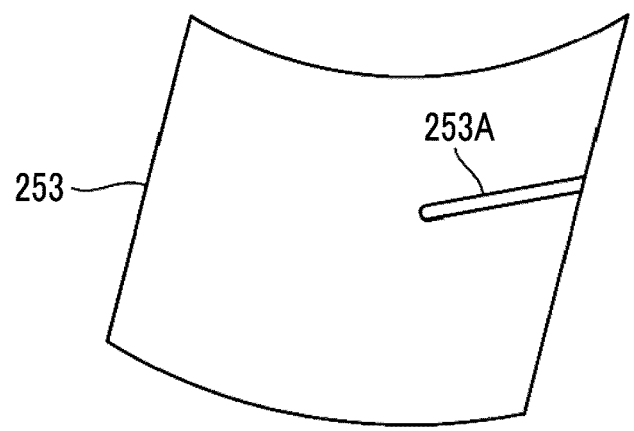
FIG. 41A shows an example of the first ultrasound image.

FIG. 41A shows the first ultrasound image 253 among the plurality of first ultrasound images 251 to 253.

The first ultrasound image 253 is obtained by performing phasing addition along the line 233 in the virtual reception direction shown in FIG. 39A. A portion 253A of the needle is included in the first ultrasound image 253.

Figure 41B:
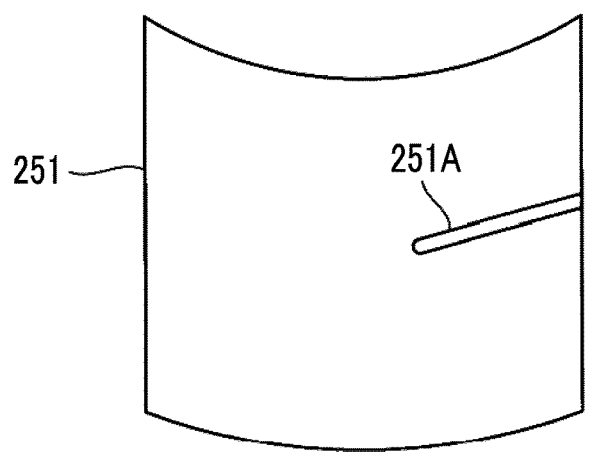
FIG. 41B shows an example of the first ultrasound image.

FIG. 41B shows the first ultrasound image 251 among the plurality of first ultrasound images 251 to 253.

The first ultrasound image 251 is obtained from the line 231 in the first direction (the virtual reception direction is also the same) shown in FIG. 37A. A portion 251A of the needle is included in the first ultrasound image 251.

Figure 41C:
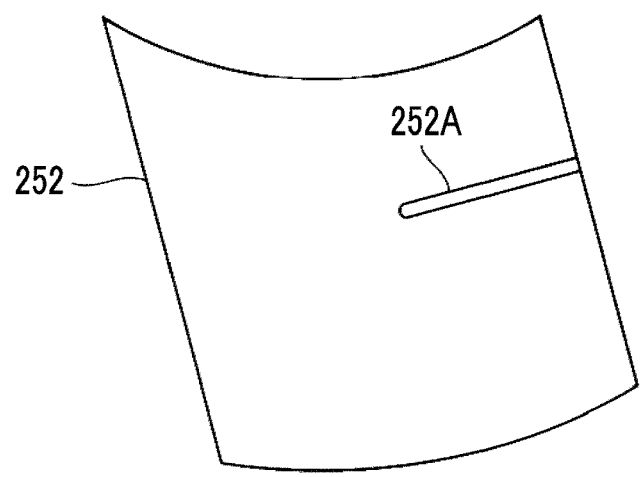
FIG. 41C shows an example of the first ultrasound image.

FIG. 41C shows the first ultrasound image 252 among the plurality of first ultrasound images 251 to 253.

The first ultrasound image 252 is obtained by performing phasing addition along the line 232 in the virtual reception direction shown in FIG. 38A. A needle portion 252A is included in the first ultrasound image 252.

By acquiring the plurality of first ultrasound images 251 to 253 in this manner, a needle image in which it is easy to see the needle is generated (newly generated, selected, or the like). Since ultrasound waves are transmitted to the subject so as to be perpendicular to the subject, the first ultrasound image 251 is suitable for displaying the tissue. The first ultrasound image 251 and the generated needle image can be combined.

Thus, even in a case where the ultrasound transducers 20 to 32 forming the ultrasound probe 6 are arranged in the arc direction, it is possible to obtain a needle image that is easy to see, as in a case where the ultrasound transducers 20 to 32 are arranged in a straight line in one direction.

What is claimed is:

1. An acoustic wave image generating apparatus, comprising:
    an acoustic wave probe having a plurality of acoustic wave transducers that transmit acoustic waves to a subject, receive acoustic wave echoes from the subject, and output acoustic wave echo signals;
    an analog/digital conversion circuit that digitally converts a plurality of acoustic wave echo signals output from the plurality of acoustic wave transducers into first acoustic wave echo data; and
    a control circuitry configured to:
        cause the acoustic wave transducers to transmit acoustic waves, which have an intensity distribution centered on a first direction from the plurality of acoustic wave transducers, while updating the plurality of acoustic wave transducers;
        set a plurality of virtual reception directions; and
        generate a plurality of first acoustic wave images by performing phasing addition of the first acoustic wave echo data, which is obtained by conversion in the analog/digital conversion circuit, along lines in the plurality of virtual reception directions.

2. The acoustic wave image generating apparatus according to claim 1,
    wherein said control circuitry generates a needle image from the plurality of first acoustic wave images.

3. The acoustic wave image generating apparatus according to claim 2,
    wherein said control circuitry calculates an evaluation value of needle likeness for each of the plurality of first acoustic wave images, and selects a first acoustic wave image having a largest calculated evaluation value as the needle image.

4. The acoustic wave image generating apparatus according to claim 3,
    wherein said control circuitry detects a region where a needle is present from each of the plurality of first acoustic wave images, and
    calculates an evaluation value of needle likeness for the region detected by said control circuitry, and selects a first acoustic wave image having a largest calculated evaluation value as the needle image.

5. The acoustic wave image generating apparatus according to claim 3,
    wherein said control circuitry aligns the plurality of first acoustic wave images by coordinate transformation.

6. The acoustic wave image generating apparatus according to claim 2,
    wherein said control circuitry generates a new needle image using the plurality of first acoustic wave images.

7. The acoustic wave image generating apparatus according to claim 2,
    wherein said control circuitry causes the acoustic wave transducers to transmit acoustic waves, which have an intensity distribution centered on a second direction from the plurality of acoustic wave transducers, while updating the plurality of acoustic wave transducers,
    the analog/digital conversion circuit digitally converts a plurality of acoustic wave echo signals, which are output from the plurality of acoustic wave transducers due to transmission of the acoustic waves having an intensity distribution centered on the second direction, into second acoustic wave echo data, and
    wherein said control circuitry generates a second acoustic wave image by performing phasing addition of the second acoustic wave echo data along a line in the second direction and combines the second acoustic wave image and the needle image are provided.

8. The acoustic wave image generating apparatus according to claim 7,
    wherein said control circuitry causes acoustic waves to be transmitted in a state in which the number of acoustic wave transducers that transmit acoustic waves having an intensity distribution centered on the first direction is larger than the number of acoustic wave transducers that transmit acoustic waves having an intensity distribution centered on the second direction.

9. The acoustic wave image generating apparatus according to claim 7,
    wherein said control circuitry combines the needle image generated by said control circuitry and the second acoustic wave image generated by said control circuitry with a predetermined weighting.

10. The acoustic wave image generating apparatus according to claim 7,
    wherein the second direction is a direction perpendicular to each of the plurality of acoustic wave transducers, and
    the first direction is a direction inclined from a direction perpendicular to each of the plurality of acoustic wave transducers.

11. The acoustic wave image generating apparatus according to claim 2,
    wherein the first direction is a direction perpendicular to each of the plurality of acoustic wave transducers, and
    wherein said control circuitry combines a third acoustic wave image generated by phasing addition along a line in a direction perpendicular to each of the plurality of acoustic wave transducers, among the plurality of first acoustic wave images, and the needle image is further provided.

12. The acoustic wave image generating apparatus according to claim 1,
    wherein a line in the first direction is included within a range of the lines in the plurality of virtual reception directions set by said control circuitry.

13. The acoustic wave image generating apparatus according to claim 12,
    wherein one of the lines in the plurality of virtual reception directions set by said control circuitry.

14. An acoustic wave image generating method, comprising:
    transmitting acoustic waves, which have an intensity distribution centered on a first direction from a plurality of acoustic wave transducers, while updating the plurality of acoustic wave transducers of an acoustic wave probe, which has the plurality of acoustic wave transducers that transmit acoustic waves to a subject, receiving acoustic wave echoes from the subject, and outputting acoustic wave echo signals;
    digitally converting, via an analog/digital conversion circuit, a plurality of acoustic wave echo signals output from the plurality of acoustic wave transducers into first acoustic wave echo data;
    setting of a plurality of virtual reception directions; and
    generating a plurality of first acoustic wave images by performing phasing addition of the first acoustic wave echo data, which is obtained by conversion in the analog/digital conversion circuit, along lines in the plurality of virtual reception directions.

\* \* \* \* \*